(12) United States Patent
Kashi et al.

(10) Patent No.: US 12,098,409 B2
(45) Date of Patent: Sep. 24, 2024

(54) PROBIOTIC BACTERIA FOR YEAST BIOETHANOL PRODUCTION

(71) Applicant: TECHNION RESEARCH & DEVELOPMENT FOUNDATION LIMITED, Haifa (IL)

(72) Inventors: Yechezkel Kashi, Hayogev (IL); Inbar Kesten, Haifa (IL); Keren Buhnik-Rosenblau, Kibbutz Usha (IL)

(73) Assignee: TECHNION RESEARCH &DEVELOPMENT FOUNDATION LIMITED, Haifa (IL)

( * ) Notice: Subject to any disclaimer, the term of this patent is extended or adjusted under 35 U.S.C. 154(b) by 0 days.

(21) Appl. No.: 17/983,665

(22) Filed: Nov. 9, 2022

(65) Prior Publication Data

US 2023/0084656 A1 Mar. 16, 2023

Related U.S. Application Data

(62) Division of application No. 17/041,090, filed as application No. PCT/IL2019/050336 on Mar. 25, 2019, now abandoned.

(60) Provisional application No. 62/647,741, filed on Mar. 25, 2018, provisional application No. 62/666,211, filed on May 3, 2018.

(51) Int. Cl.
| | | |
|---|---|---|
| *C12P 7/10* | (2006.01) | |
| *C12N 1/16* | (2006.01) | |
| *C12N 1/18* | (2006.01) | |
| *C12N 1/20* | (2006.01) | |
| *C12N 9/28* | (2006.01) | |
| *C12N 9/34* | (2006.01) | |
| *C12N 9/42* | (2006.01) | |
| *C12N 9/54* | (2006.01) | |
| *C12P 7/06* | (2006.01) | |
| *C12R 1/07* | (2006.01) | |
| *C12R 1/38* | (2006.01) | |
| *C12R 1/84* | (2006.01) | |
| *C12R 1/85* | (2006.01) | |

(52) U.S. Cl.
CPC ............. *C12P 7/10* (2013.01); *C12N 9/2417* (2013.01); *C12N 9/2428* (2013.01); *C12N 9/2437* (2013.01); *C12N 9/54* (2013.01); *C12P 7/065* (2013.01); *C12N 1/165* (2021.05); *C12N 1/185* (2021.05); *C12N 1/205* (2021.05); *C12P 2203/00* (2013.01); *C12R 2001/07* (2021.05); *C12R 2001/38* (2021.05); *C12R 2001/84* (2021.05); *C12R 2001/85* (2021.05); *C12Y 302/01001* (2013.01); *C12Y 302/01003* (2013.01); *C12Y 302/01004* (2013.01)

(58) Field of Classification Search
CPC ...... C12N 9/2417; C12N 9/2428; C12N 9/54; C12N 1/165; C12N 1/185; C12N 1/205; C12N 1/20; C12P 7/065; C12P 2203/00; C12R 2001/85; C12R 2001/07; C12R 2001/84; C12R 2001/38; C12Y 302/01004; C12Y 302/01001; C12Y 302/01003; Y02E 50/10
See application file for complete search history.

(56) References Cited

U.S. PATENT DOCUMENTS

| | | | |
|---|---|---|---|
| 8,802,421 | B2 | 8/2014 | White |
| 2010/0098805 | A1 | 4/2010 | Vykhodtsev |
| 2018/0264052 | A1 | 9/2018 | Lewis et al. |

FOREIGN PATENT DOCUMENTS

| | | | | |
|---|---|---|---|---|
| JP | 5050236 | * | 10/2012 | ................ C12P 7/06 |
| JP | 5050236 B2 | * | 10/2012 | ................ C12P 7/06 |

OTHER PUBLICATIONS

Teng, Po Yun, et al. Effects of solid-state fermented wheat bran by Bacillus amyloliquefaciens and *Saccharomyces cerevisiae* on growth performance and intestinal microbiota in broiler chickens. Italian Journal of Animal Science, 2017; Dowloaded Jun. 11, 2017 from:http://dx.doi.org/10.1080/1828051X.2017.1299597; Retrieved Aug. 24, 2021.

Zabed, H., et al. Bioethanol production from renewable sources: Current perspectives and technological progress. Renewable and Sustainable Energy Reviews, 2017; Retrieved Aug. 24, 2021 from: http://dx.doi.org/10.1016/j.rser.2016.12.076.

Grossman AD, Lewis T, Levin N, & DeVivo, R. Suppressors of a spo0A missense mutation and their effects on sporulation in Bacillus subtilis. Biochimie. 1992. Retrieved Aug. 24, 2021 from: https://www.sciencedirect.com/science/article/abs/pii/030090849290140A?via%3Dihub.

Masel, J. & Maughan H. Mutations leading to loss of sporulation ability in Bacillus subtilis are sufficiently frequent to favor genetic canalization. Genetics. 2007. Retrieved Aug. 24, 2021; DOI: 10.1534/genetics.106.065201.

Quisel J.D. & Grossman A.D., Control of sporulation gene expression in Bacillus subtilis by the chromosome partitioning proteins Soj (ParA) and Spo0J (ParB). J Bacteriol. 2000. Retrieved Aug. 24, 2021; DOI: 10.1128/JB.182.12.3446-3451.2000.

Higgins, D. & Dworkin J., Recent progress in Bacillus subtilis sporulation. FEMS Microbiol Rev. 2012. Retrieved Aug. 24, 2021; doi:10.1111/j.1574-6976.2011.00310.x.

Widderich, et al., Salt-sensitivity of σ(H) and Spo0A prevents sporulation of Bacillus subtilis at high osmolarity avoiding death during cellular differentiation. Mol Microbiol. 2016. Retrieved Aug. 24, 2021; doi:10.1111/mmi.13304.

Rich et al., Resolving bacterial contamination of fuel ethanol fermentations with beneficial bacteria—An alternative to antibiotic treatment, Bioresource Technology, vol. 247, 2018. Retrieved Aug. 24, 2021 from: http://dx.doi.org/10.1016/j.biortech.2017.09.067.

(Continued)

*Primary Examiner* — Ganapathirama Raghu
(74) *Attorney, Agent, or Firm* — The Roy Gross Law Firm, LLC; Roy Gross

(57) ABSTRACT

The present invention is directed to compositions comprising hydrolase-secreting bacteria and fermenting microorganisms and use thereof, such as for fermentative production of ethanol.

10 Claims, 7 Drawing Sheets

(56) References Cited

OTHER PUBLICATIONS

Lucena et al., Diversity of lactic acid bacteria of the bioethanol process. BMC Microbiol. 2010; 10(1):298. Retrieved Aug. 24, 2021 from: http://www.biomedcentral.com/1471-2180/10/298.

Beckner et al., Microbial contamination of fuel ethanol fermentations. Lett Appl Microbiol. 2011;53(4):387-394. Retrieved Aug. 24, 2021; doi:10.1111/j.1472-765X.2011.03124.x.

Brexó R.P. & Sant'Ana, A.S., Impact and Significance of Microbial Contamination During Fermentation for Bioethanol Production. Renew Sustain Energy Rev. 2017;73. Retrieved Aug. 24, 2021; doi: 10.1016/j.rser.2017.01.151.

Bonatelli et al., Characterization of the contaminant bacterial communities in sugarcane first-generation industrial ethanol production. FEMS Microbiol Lett. Sep. 15, 2017;364(17). Retrieved Aug. 24, 2021; doi: 10.1093/femsle/fnx159.

Narendranath N.V. & Power, R., Relationship between pH and medium dissolved solids in terms of growth and metabolism of lactobacilli and *Saccharomyces cerevisiae* during ethanol production. Appl Environ Microbiol. May 2005;71(5):2239-43. Retrieved Aug. 24, 2021; doi: 10.1128/AEM.71.5.2239-2243.2005.

Thomas et al., Influence of medium buffering capacity on inhibition of *Saccharomyces cerevisiae* growth by acetic and lactic acids. Appl Environ Microbiol. Apr. 2002;68(4):1616-23. Retrieved Aug. 24, 2021; DOI: 10.1128/AEM.68.4.1616-1623.2002.

Skinner-Nemec et al., Biofilm formation by bacterial contaminants of fuel ethanol production. Biotechnol Lett. Mar. 2007;29(3):379-83. Retrieved Aug. 24, 2021; DOI 10.1007/s10529-006-9250-0.

Teusink B. & Smid E.J., Modelling strategies for the industrial exploitation of lactic acid bacteria. Nat Rev Microbiol. Jan. 2006;4(1):46-56. Retrieved Aug. 24, 2021; doi:10.1038/nrmicro1319.

Bothast, R.J. & Schlicher, M.A., Biotechnological processes for conversion of corn into ethanol. Appl Microbiol Biotechnol. Apr. 2005;67(1):19-25. Retrieved Aug. 24, 2021; DOI 10.1007/s00253-004-1819-8.

Larsen et al., Characterization of *Bacillus* spp. strains for use as probiotic additives in pig feed. Appl Microbiol Biotechnol. Feb. 2014;98(3):1105-18. Retrieved Aug. 24, 2021; DOI 10.1007/s00253-013-5343-6.

Altschul S.F. et al., Gapped BLAST and PSI-BLAST: a new generation of protein database search programs. Nucleic Acids Res. Sep. 1, 1997;25(17):3389-402. Retrieved Aug. 24, 2021; doi: 10.1093/nar/25.17.3389.

Dong S.J. et al., Regulation of Lactobacillus plantarum contamination on the carbohydrate and energy related metabolisms of *Saccharomyces cerevisiae* during bioethanol fermentation. Int J Biochem Cell Biol. Nov. 2015;68:33-41. Retrieved Aug. 24, 2021; DOI: 10.1016/j.biocel.2015.08.010.

Slepecky, Ralph & Hemphill, H . . . (2006). The Genus *Bacillus* Nonmedical. Retrieved Aug. 24, 2021; DOI: 10.1007/0-387-30744-3_16.

Teotia, S. et al., One-step purification of glucoamylase by affinity precipitation with alginate. J Mol Recognit. Sep.-Oct. 2001;14(5):295-9. Retrieved Aug. 24, 2021; DOI:10.1002/jmr.540.

Cruz Ramos et al.,. Fermentative metabolism of Bacillus subtilis: physiology and regulation of gene expression. J Bacteriol. Jun. 2000;182(11):3072-80. Retrieved Aug. 24, 2021; doi: 10.1128/JB.182.11.3072-3080.2000.

Vu et al., Batch and fed-batch fermentation of Bacillus thuringiensis using starch industry wastewater as fermentation substrate. Bioprocess Biosyst Eng. Aug. 2010;33(6):691-700. Retrieved Aug. 24, 2021; DOI 10.1007/s00449-009-0391-0.

Anto, Hema et al., (2006). Alpha Amylase Production by Bacillus cereus MTCC 1305 Using Solid-State Fermentation. Food Technology and Biotechnology. 44. Retrieved Aug. 24, 2021 from: https://www.researchgate.net/publication/242526455_Alpha_Amylase_Production_by_Bacillus_cereus_MTCC_1305_Using_Solid-State_Fermentation.

Belyea et al.,Composition of corn and distillers dried grains with solubles from dry grind ethanol processing. Bioresour Technol. Sep. 2004;94(3):293-8. Retrieved Aug. 24, 2021; doi:10.1016/j.biortech.2004.01.001.

May B.K. & Elliott W.H., Characteristics of extracellular protease formation by Bacillus subtilis and its control by amino acid repression. Biochim Biophys Acta. May 21, 1968;157(3):607-15. Retrieved Aug. 24, 2021; 10.1016/0005-2787 (68)90158-5.

Antelmann et al . . . A proteomic view on genome-based signal peptide predictions. Genome Res. Sep. 2001;11(9):1484-502. Retrieved Aug. 24, 2021 from: http://www.genome.org/cgi/doi/10.1101/gr.182801.

Wang et al., (2015). A new potential secretion pathway for recombinant proteins in Bacillus subtilis. Microbial cell factories. 14. 179. Retrieved Aug. 24, 2021; DOI 10.1186/s12934-015-0374-6.

Bendtsen et al., Non-classical protein secretion in bacteria. BMC Microbiol. Oct. 7, 2005;5:58. Retrieved Aug. 24, 2021 from: http://www.biomedcentral.com/1471-2180/5/58.

Tjalsma H. et al. Signal peptide-dependent protein transport in Bacillus subtilis: a genome-based survey of the secretome. Microbiol Mol Biol Rev. Sep. 2000;64(3):515-47. Retrieved Aug. 24, 2021; doi: 10.1128/MMBR.64.3.515-547.2000.

Simonen, Marjo & Ilkka Palva. "Protein secretion in Bacillus species." Microbiological Reviews 57.1 (1993): 109-137. Retrieved Aug. 24, 2021 from: https://www.researchgate.net/publication/14735715_Protein_secretion_in_Bacillus_species.

Brockmeier, Ulf. New strategies to optimize the secretion capacity for heterologous proteins in Bacillus subtilis. 2006. Dissertation.

Sukon Tantipaibulvut et al: "Ethanol Production from Desizing Wastewater using Co-Culture of Bacillus subtilis and *Saccharomyces cerevisiae*", Energy Procedia 79 ( 2015 ) 1001-1007.

Zahia Djenane et al: "Assessment of the Antimicrobial Activity and the Entomocidal Potential of Bacillus thuringiensis Isolates from Algeria", Toxins 2017, 9, 139.

Promon SK., "Studies on Isolation of Yeasts from Natural Sources for Bioethanol production from Vegetable Peels and the Role of Cellulose Degrading Bacteria (Bacillus subtilis) on Ethanol Production". Thesis submitted to BRAC Univ., 2015, Dhaka, Bangladesh, pp. 1-70. (Year: 2015).

Li et al., Characterization of bacteria and yeasts isolated from traditional fermentation starter (Fen-Daqu) through a 1 H NM R-based metabolomics approach. Food Micro Biol., 2018, vol. 76: 11-20. (Year: 2018).

Zheng et al., Daqu—A Traditional Chinese Liquor Fermentation Starter. J. Inst. Brew., 2011, vol. 117(1 ): 82-90. (Year: 2011).

Zheng et al., Complex microbiota of a Chinese "Fen" liquor fermentation starter (Fen-Daqu), revealed by culture-dependent and culture-independent methods. Food Microbial., 2012, vol. 31: 293-300. (Year: 2012).

Zheng et al., Microbiota dynamics related to environmental conditions during the fermentative production of Fen-Daqu, a Chinese industrial fermentation starter. Int. J. Food Micrbiol., 2014, vol. 182-183: 57-62. (Year: 2014).

Dixon B.R.E.A., in Vitro Evaluation of the Potential for Select Bacteria and Yeast as Probiotics in Poultry Production. M.Sc., Thesis, 2013, Tennessee State Univ., pp. 1-90. (Year: 2013).

Teng et al., Administration of Bacillus Amyloliquefaciens and *Saccharomyces cerevisiae* as Direct-Fed Microbials Improves Intestinal Microflora and Morphology in Broiler Chickens. The J. Poultry Sci., 2016, pp. 1-35; Advance publication date Nov. 25, 2016. (Year: 2016).

Viljoen BC., Chapter 4, Yeast Ecological Interactions. Yeast-Yeast, Yeast-Bacteria, Yeast-Fungi Interactions and Yeasts as Biocontrol Agents. The Yeast Handbook, Amparo Querol, Graham H. Fleet (Eds.): Yeasts in Food and Beverages, Springer-Verlag Berlin Heidelberg 2006, pp. 83-110. (Year: 2006).

PCT International Search Report for International Application No. PCT/IL2019/050336, mailed May 29, 2019, 3pp.

PCT Written Opinion for International Application No. PCT/IL2019/050336, mailed May 29, 2019, 7pp.

PCT International Preliminary Report on Patentability for International Application No. PCT/IL2019/050336, issued Sep. 29, 2020, 8pp.

* cited by examiner

PROBIOTIC BACTERIA FOR YEAST BIOETHANOL PRODUCTION

CROSS-REFERENCE TO RELATED APPLICATIONS

This application is a Divisional Application of U.S. patent application Ser. No. 17/041,090, filed Sep. 24, 2020, which is a National Phase of PCT Patent Application No. PCT/IL2019/050336 having International filing date of Mar. 25, 2019, which claims the benefit of priority of U.S. Provisional Patent Application Nos. 62/647,741, filed Mar. 25, 2018, and 62/666,211, filed May 3, 2018, the contents of which are incorporated herein by reference in their entirety.

FIELD OF THE INVENTION

The present invention is in the field of biofuel production, in particular fermentative production of alcohols such as ethanol.

BACKGROUND OF THE INVENTION

Bioethanol facilities suffer greatly from contaminations caused by bacteria and fungi, and rely heavily on antibiotics as a mean to control them. Bacterial contaminants utilize the much-needed glucose while decreasing pH, thus impairing yeast ethanol production. For this reason the ethanol industry continuously fight bacterial contamination with the addition of antibiotics. However, some contaminating bacterial species secrete amylolytic enzymes, thus aiding starch hydrolysis. Similarly, bacterial proteases can create an influx of peptides essential for yeast maintenance during corn fermentation. Other species might also present antibacterial powers against harming contaminants.

Ethanol producers are required to increase antibiotics concentrations, due to the development of resistant bacteria, making their production less economic. Biofilm producing bacteria are highly tolerant towards antibiotics, hence biofuel plants must repeatedly undergo rigorous cleaning downtimes, in which they suffer great financial losses. New solutions are being sought after, particularly the use of natural antibacterial compounds, yet these solutions are still under development and are not cost-effective.

SUMMARY OF THE INVENTION

The present invention provides a composition and a kit comprising at least one hydrolase-secreting bacteria and at least one fermenting microorganism. The invention further provides a fermentation method using the composition described herein.

In some embodiments, the composition comprises at least one hydrolase-secreting bacteria and at least one fermenting microorganism, in a ratio ranging from 1:1-1:1000.

In some embodiments, the composition comprises at least one hydrolase-secreting bacteria in a ratio ranging from $1 \times 10^3$-$1 \times 10^9$ CFU/ml, and the at least one fermenting microorganism is present in a ratio ranging from $1 \times 10^6$-$1 \times 10^9$ CFU/ml.

In some embodiments, the hydrolase-secreting bacteria is an amylase-secreting bacterium, a protease-secreting bacteria, a cellulase-secreting bacteria and a combination thereof.

In some embodiments, said bacteria has a pH-regulating property in the range of 3.5 to 7.

In some embodiments, said bacteria maintains secretion of any one of amylase, protease and cellulase, and combinations thereof, in a solution having a pH in the range of 3.5 to 7.

In some embodiments, said bacteria has an antimicrobial activity.

In some embodiments, the composition of the present invention, further comprises a bacteria having an antimicrobial activity.

In some embodiments, the composition of the present invention, further comprises an enzyme preparation.

In some embodiments, the growth of said bacteria is inhibited when exposed to ethanol at a concentration of more than 7% (V/V).

In some embodiments, the composition of the present invention increases concertation of ethanol production by at least 0.1% (V/V).

In some embodiments, said bacteria is selected from the genera *Bacillus, Pseudomonas* or a combination thereof. In some embodiments, said bacteria is a bacteria having one or more characteristics selected from amylase-secreting bacteria, a protease-secreting bacteria and antimicrobial activity.

In some embodiments, said fermenting microorganism is selected from *Saccharomyces, Pichia* or a combination thereof. In some embodiments, the fermenting microorganism (e.g., yeast) is suitable for alcohol production.

According to one aspect, the present invention provides a kit comprising at least one bacteria and at least one fermenting microorganism wherein the at least one bacteria is a hydrolase-secreting bacteria.

In some embodiments, the kit comprises instructions for: (i) mixing at least one hydrolase-secreting bacteria and at least one fermenting microorganism in a ratio from 1:1 to 1:1000; and (ii) applying the composition formed by mixing at least one bacteria and at least one fermenting microorganism to a fermentation method.

In some embodiments, at least one bacteria and at least one fermenting microorganism are packaged within a box or container.

In some embodiments, said composition formed by mixing at least one bacteria and at least one fermenting microorganism maintains the amylase secretion and/or protease secretion in a solution having a pH in the range of 3.5 to 7.

In some embodiments, said composition formed by mixing at least one bacteria and at least one fermenting microorganism increases the concentration of bioethanol production by at least 0.1% (V/V).

According to one aspect, the present invention provides a fermentation method comprising providing a composition comprising (i) at least one hydrolase-secreting bacteria; (ii) at least one fermenting microorganism, and (iii) a biomass containing fermentable carbon source, and maintaining the composition under fermentable conditions suitable for producing at least one product alcohol.

In some embodiments, providing is providing the hydrolase-secreting bacteria and the at least one fermenting microorganism in a ratio ranging from 1:1 to 1:1000.

In some embodiments, providing is providing the hydrolase-secreting bacteria in a ratio ranging from $1 \times 10^3$-$1 \times 10^9$ CFU/ml, and the at least one fermenting microorganism in a ratio ranging from $1 \times 10^6$-$1 \times 10^9$ CFU/ml.

In some embodiments, the fermentation method has at least 0.1% (V/V) increase in the concentration or the rate of bioethanol production.

In some embodiments, the pH of said fermentation method is substantially maintained in the range of 3.5 to 7.

In some embodiments, the at least one bacteria is an amylase-secreting bacteria, a protease-secreting bacteria, a cellulase-secreting bacteria, anti-microbial bacteria and a combination thereof. In some embodiments, the growth of said hydrolase-secreting bacteria is inhibited when exposed to ethanol at a concentration of more than 7% (V/V). In some embodiments, the bacteria maintains the secretion of any one of amylase, protease and cellulase, and combinations thereof, in a solution having a pH in the range of 3.5 to 7.

In some embodiments, the method further comprises providing to the composition a bacteria having an antimicrobial activity. In some embodiments, the method further comprises providing to the composition an enzyme preparation.

In some embodiments, the fermentation method of the present invention is shortened by at least 30 minutes, or at least 60 minutes, as compared to a similar fermentation method devoid of the hydrolase-secreting bacteria.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
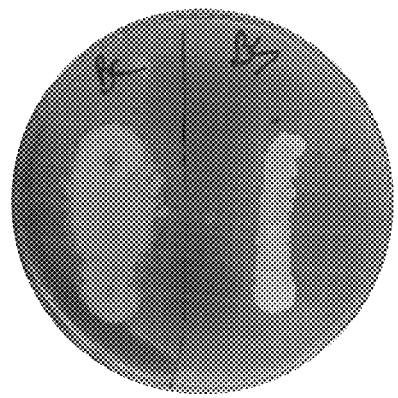
FIG. 1 Presents an agar plate where a starch degradation test was performed for control strains *Bacillus cereus* ATCC 11778 (left side of the place indicated with BC) and *Bacillus subtilis* ATCC 6633 (right side of the plate indicated with BS). Plates were incubated at 32.5° C. and reviewed after 48 hours.

According to some embodiments, the present invention provides a composition comprising at least one hydrolase-secreting bacteria and at least one fermenting microorganism.

In some embodiments, the composition comprises at least one hydrolase-secreting bacteria and at least one fermenting microorganism, in a ratio ranging from 1:1-1:1000.

In some embodiments, the composition comprises at least one hydrolase-secreting bacteria in a ratio ranging from $1\times10^3$-$1\times10^9$ CFU/ml. In some embodiments, the composition comprises the at least one fermenting microorganism in a ratio ranging from $1\times10^6$-$1\times10^9$ CFU/ml In some embodiments, the composition comprises at least one bacteria and at least one fermenting microorganism in a ratio of $1\times10^3$:$1\times10^6$ CFU/ml. In some embodiments, the composition comprises at least one bacteria and at least one fermenting microorganism in a ratio of $1\times10^3$:$1\times10^7$ CFU/ml. In some embodiments, the composition comprises at least one bacteria and at least one fermenting microorganism in a ratio of $1\times10^4$:$1\times10^7$ CFU/ml.

In some embodiments, the composition comprises at least one bacteria and at least one fermenting microorganism in a ratio ranging from $1\times10^3$:$1\times10^6$ to $1\times10^8$: $1\times10^8$ CFU/ml. In some embodiments, the composition comprises at least one bacteria and at least one fermenting microorganism in a ratio ranging from $1\times10^4$:$1\times10^7$ to $1\times10^8$: $1\times10^8$ CFU/ml.

In some embodiments, at least one bacteria is an amylase-secreting bacteria. In some embodiments, at least one bacteria is a protease-secreting bacteria. In some embodiments, at least one bacteria is an amylase- and protease-secreting bacteria.

In some embodiments, at least one bacteria is a glycosylase-secreting bacteria. In some embodiments, at least one bacteria is a peptidase-secreting bacteria. In some embodiments, at least one hydrolase-secreting bacteria is selected from a list of a phytase, cellulase, hemicellulase, ligninase, cellobiosidases, protease, aminopeptidase, α-amylase, β-amylase, carboxypeptidase, chitinase, cutinase, cyclodextrin, glucanotransferase, deoxyribonuclease, esterase, α-galactosidase, β-galactosidase, glucoamylase, α-glucosidase, β-glucosidase, invertase, isomerase, laccase, lipase, mannosidase, oxidase, pectinase, peptidoglutaminase, peroxidase, polyphenoloxidase, nuclease, transglutaminase, xylanase, pullulanase, isoamylase, carrageenase, or a combination thereof.

In some embodiments, the composition comprises at least one bacteria having an antimicrobial activity. It should be understood that the term antimicrobial activity includes activity towards niche-occupation.

In some embodiments, the composition further comprises bacteria having an antimicrobial activity. In some embodiments, the composition further comprises bacteria having an antimicrobial activity against gram positive bacteria, gram negative bacteria or a combination thereof.

In some embodiments, the growth of said bacteria is inhibited when exposed to ethanol at a concentration of more than 7% (V/V). In some embodiments, the growth of said bacteria is inhibited when exposed to ethanol at a concentration of more than 7.5% (V/V). In some embodiments, the growth of said bacteria is inhibited when exposed to ethanol at a concentration of more than 8% (V/V). In some embodiments, the growth of said bacteria is inhibited when exposed to ethanol at a concentration of more than 10% (V/V). In some embodiments, the growth of said bacteria is inhibited when exposed to ethanol at a concentration of more than 12% (V/V). In some embodiments, the growth of said bacteria is inhibited when exposed to ethanol at a concentration of more than 15% (V/V). In some embodiments, the growth of said bacteria is inhibited when exposed to ethanol at a concentration of more than 17% (V/V).

In some embodiments, said bacteria undergo lysis when exposed to ethanol at a concentration of more than 7% (V/V). In some embodiments said bacteria undergo lysis when exposed to ethanol at a concentration of more than 7.5% (V/V). In some embodiments said bacteria undergo lysis when exposed to ethanol at a concentration of more than 8% (V/V). In some embodiments said bacteria undergo lysis when exposed to ethanol at a concentration of more than 10% (V/V). In some embodiments said bacteria undergo lysis when exposed to ethanol at a concentration of more than 12% (V/V). In some embodiments said bacteria undergo lysis when exposed to ethanol at a concentration of more than 15% (V/V). In some embodiments said bacteria undergo lysis when exposed to ethanol at a concentration of more than 17% (V/V).

In some embodiments, said composition increases concertation of ethanol production by at least 0.1% (V/V). In some embodiments, said composition increases concertation of ethanol production by at least 0.5% (V/V). In some embodiments, said composition increases concertation of ethanol production by at least 1% (V/V). In some embodiments, said composition increases concertation of ethanol production by at least 2% (V/V). In some embodiments, said composition increases concertation of ethanol production by at least 3% (V/V). In some embodiments, said composition increases concertation of ethanol production by at least 4% (V/V). In some embodiments, said composition increases concertation of ethanol production by at least 5% (V/V). In some embodiments, said composition increases concertation of ethanol production by at least 6% (V/V). In some embodiments, said composition increases concertation of ethanol production by at least 7% (V/V). In some embodiments, said composition increases concertation of ethanol production by at least 8% (V/V). In some embodiments, said composition increases concertation of ethanol production by at least 9% (V/V). In some embodiments, said composition increases concertation of ethanol production by at least 10% (V/V).

In some embodiments, said composition increases concertation of ethanol production by a range of 0.1% to 1% (V/V). In some embodiments, said composition increases concertation of ethanol production by a range of 0.1% to 2% (V/V). In some embodiments, said composition increases concertation of ethanol production by a range of 0.1% to 5% (V/V). In some embodiments, said composition increases concertation of ethanol production by a range of 0.1% to 10% (V/V). In some embodiments, said composition increases concertation of ethanol production by a range of 0.1% to 20% (V/V). In some embodiments, said composition increases concertation of ethanol production by a range of 0.5% to 2% (V/V). In some embodiments, said composition increases concertation of ethanol production by a range of 1% to 2% (V/V). In some embodiments, said composition increases concertation of ethanol production by a range of 0.5% to 2% (V/V). In some embodiments, said composition increases ethanol production by a range of 1% to 5% (V/V). In some embodiments, said composition increases concertation of ethanol production by a range of 1% to 10% (V/V). In some embodiments, said composition increases concertation of ethanol production by a range of 1% to 20% (V/V). In some embodiments, said composition increases concertation of ethanol production by a range of 2% to 5% (V/V). In some embodiments, said composition increases concertation of ethanol production by a range of 5% to 10% (V/V). In some embodiments, said composition increases concertation of ethanol production by a range of 5% to 20% (V/V). In some embodiments, said composition increases concertation of ethanol production by a range of 10% to 20% (V/V).

In some embodiments, the composition further comprises an enzyme preparation.

As used herein, the term "enzyme preparation" refers to a composition containing one enzyme or a mixture of enzymes that efficiently catalyze a hydrolysis reaction under conditions suitable for fermentation.

In some embodiments, the enzyme preparation can be used in the ethanol production processes known in the art.

In some embodiments, the enzyme preparation is a hydrolase.

In some embodiments, the enzyme preparation contains an enzyme selected from glucoamylase, alpha-amylase, protease, or any combination thereof.

In some embodiments, the enzyme preparation composition contains the same hydrolase as secreted by the bacteria. In some embodiments, the enzyme preparation composition contains a hydrolase which is not secreted by the bacteria.

In some embodiments, the enzyme preparation is used to improve the ability of hydrolase-secreting bacteria to increase the concentration of ethanol production in a fermentation process.

Fermentation process conducted with the "enzyme preparation" means that an enzyme is added to the fermentation process from an external source; i.e., a solution of an enzyme exogenous to the fermentation process is added to the process.

The effective amount of the enzyme preparation to be included in the composition and methods of the present invention can be readily determined by one skilled in the art. In some embodiments, the amount of the enzyme used in the composition and method of the invention (i.e., combined with the hydrolase-secreting bacteria) is not more than 95%, not more than 75%, not more than 50%, not more than 40%, not more than 30%, not more than 25%, not more than 20%, not more than 15%, not more than 10%, or not more than 5% of the enzyme used under a fermentation reaction devoid of the hydrolase-secreting bacteria.

In some embodiment, combination of an enzyme preparation and the hydrolase-secreting bacteria provides increased bioethanol production (e.g., increase production rates).

In some embodiments, the bacteria is selected from the genera *Bacillus, Pseudomonas* or a combination thereof.

In some embodiments, the fermenting microorganism is yeast.

In some embodiments, the fermenting microorganism is selected from *Saccharomyces, Pichia* or a combination thereof.

In some embodiments, said bacteria has a pH-regulating property in the range of 3.5 to 7. In some embodiments, said bacteria has a pH-regulating property in the pH range of 5 to 7. In some embodiments, said bacteria has a pH-regulating property in the range of 5 to 5.9. In some embodiments, said bacteria has a pH-regulating property in the range of 5.5 to 7.

In some embodiments, said bacteria has a pH-regulating property in the range of 3.5 to 6. In some embodiments, said bacteria has a pH-regulating property in the pH range of 5 to 6. In some embodiments, said bacteria has a pH-regulating property in the range of 5 to 5.9. In some embodiments, said bacteria has a pH-regulating property in the range of 5.5 to 6.

In some embodiments, said bacteria maintains the amylase secretion and/or protease secretion in a solution having a pH in the range of 3.5 to 7. In some embodiments, said bacteria maintains the amylase secretion and/or protease secretion in a solution having a pH in the range of 5 to 7. In some embodiments, said bacteria maintains the amylase secretion and/or protease secretion in a solution having a pH in the range of 5 to 5.9. In some embodiments, said bacteria maintains the amylase secretion and/or protease secretion in a solution having a pH in the range of 5.5 to 6.

The Method

According to some embodiments, the present invention provides a fermentation method comprising maintaining the composition of the present invention, and a biomass containing fermentable carbon source, under fermentable conditions producing at least one product alcohol.

In some embodiments the at least one product alcohol is a C1 to C8 alkyl alcohol. In some embodiments, the at least one product alcohol is a C2 to C8 alkyl alcohol. In some embodiments, the at least one product alcohol is C2 to C5 alkyl alcohol.

In some embodiments, at least one product alcohol is ethanol or butanol.

According to some embodiments, the biomass may be derived from a single source, or biomass can comprise a mixture derived from more than one source; for example, biomass could comprise a mixture of corn cobs and corn stover, or a mixture of grass and leaves.

In some embodiments, the fermentation method has at least 0.1% (V/V) increase in concentration of bioethanol production. In some embodiments, the fermentation method has at least 0.5% (V/V) increase in concentration of bioethanol production. In some embodiments, the fermentation method has at least 1% (V/V) increase in concentration of bioethanol production. In some embodiments, the fermentation method has at least 3% (V/V) increase in concentration of bioethanol production. In some embodiments, the fermentation method has at least 5% (V/V) increase in concentration of bioethanol production. In some embodiments, the fermentation method has at least 10% (V/V) increase in concentration of bioethanol production. In some embodiments, the fermentation method has at least 15% (V/V) increase in concentration of bioethanol production. In some embodiments, the fermentation method has at least 20% (V/V) increase in concentration of bioethanol production.

In some embodiments, the fermentation method has an increase in concentration of bioethanol production by a range of 0.1% to 2% (V/V). In some embodiments, the fermentation method has an increase in concentration of bioethanol production by a range of 0.1% to 5% (V/V). In some embodiments, the fermentation method has an increase in concentration of bioethanol production by a range of 0.1% to 10% (V/V). In some embodiments, the fermentation method has an increase in concentration of bioethanol production by a range of 0.1% to 20% (V/V). In some embodiments, the fermentation method has an increase in concentration of bioethanol production by a range of 0.5% to 2% (V/V), 0.5% to 5% (V/V), 0.5% to 5% (V/V), 0.5% to 10% (V/V), or 0.5% to 20% (V/V). In some embodiments, the fermentation method has an increase in concentration of bioethanol production by a range of 1% to 10% (V/V). In some embodiments, the fermentation method has an increase in concentration of bioethanol production by a range of 1% to 20% (V/V). In some embodiments, the fermentation method has an increase in concentration of bioethanol production by a range of 2% to 5% (V/V). In some embodiments, the fermentation method has an increase in concentration of bioethanol production by a range of 5% to 10% (V/V). In some embodiments, the fermentation method has an increase in concentration of bioethanol production by a range of 5% to 20% (V/V). In some embodiments, the fermentation method has an increase in concentration of bioethanol production by a range of 10% to 20% (V/V).

In some embodiments, the pH of said the fermentation method is substantially maintained in the range of 3.5 to 7. In some embodiments, the pH of said the fermentation method is substantially maintained in the range of 5 to 7. In some embodiments, the pH of said the fermentation method is substantially maintained in the range of 5 to 5.9. In some embodiments, the pH of said the fermentation method is substantially maintained in the range of 5.5 to 7.

The Kit

According to some embodiments, the present invention provides a kit comprising at least one bacteria and at least one fermenting microorganism, wherein the at least one bacteria is a hydrolase-secreting bacteria.

In some embodiments, the kit comprises at least one bacteria and at least one fermenting microorganism, wherein the at least one bacteria is selected from an amylase-secreting bacteria, a protease-secreting bacteria, and a combination thereof.

In some embodiments, the kit comprises one amylase- and protease-secreting bacteria and one fermenting microorganism. In some embodiments, the kit comprises one amylase-secreting bacteria, one protease-secreting bacteria and one fermenting microorganism. In some embodiments, the kit comprises one amylase- and protease-secreting bacteria, one amylase-secreting bacteria and one fermenting microorganism. In some embodiments, the kit comprises one amylase- and protease-secreting bacteria, one protease-secreting bacteria and one fermenting microorganism.

According to some embodiments, the kit is utilized by mixing at least one bacteria and at least one fermenting microorganism and applying the composition formed by mixing at least one bacteria and at least one fermenting microorganism to a fermentation method.

In some embodiments, the kit comprises instructions for mixing at least one bacteria and one fermenting microorganism in a ratio of 1:1 to 1:1000. In some embodiments, the kit comprises instructions for providing the hydrolase-secreting bacteria in a ratio ranging from $1\times10^3$-$1\times10^9$ CFU/ml, and the at least one fermenting microorganism in a ratio ranging from $1\times10^6$-$1\times10^9$ CFU/ml.

In some embodiments, said composition formed by mixing at least one bacteria and at least one fermenting microorganism maintains the amylase secretion and/or protease secretion in a solution having a pH in the range of 3.5 to 7. In some embodiments, said composition formed by mixing at least one bacteria and at least one fermenting microorganism maintains the amylase secretion and/or protease secretion in a solution having a pH in the range of 5 to 7. In some embodiments, said composition formed by mixing at least one bacteria and at least one fermenting microorganism maintains the amylase secretion and/or protease secretion in a solution having a pH in the range of 5 to 5.9. In some embodiments, said composition formed by mixing at least one bacteria and at least one fermenting microorganism maintains the amylase secretion and/or protease secretion in a solution having a pH in the range of 5.5 to 7.

In some embodiments, said composition formed by mixing at least one bacteria and at least one fermenting microorganism increases ethanol production by at least 0.1% (V/V). In some embodiments, said composition formed by mixing at least one bacteria and at least one fermenting microorganism increases ethanol production by at least 1% (V/V). In some embodiments, said composition formed by mixing at least one bacteria and at least one fermenting microorganism increases ethanol production by at least 3% (V/V). In some embodiments, said composition formed by mixing at least one bacteria and at least one fermenting microorganism increases ethanol production by at least 5% (V/V). In some embodiments, said composition formed by mixing at least one bacteria and at least one fermenting microorganism increases ethanol production by at least 10% (V/V). In some embodiments, said composition formed by mixing at least one bacteria and at least one fermenting microorganism increases ethanol production by at least 15% (V/V). In some embodiments, said composition formed by mixing at least one bacteria and at least one fermenting microorganism increases ethanol production by at least 20% (V/V).

In some embodiments, said composition formed by mixing at least one bacteria and at least one fermenting microorganism increases ethanol production by a range of 0.1% to 2% (V/V). In some embodiments, said composition formed by mixing at least one bacteria and at least one fermenting microorganism increases ethanol production by a range of 1% to 2% (V/V). In some embodiments, said composition formed by mixing at least one bacteria and at least one fermenting microorganism increases ethanol production by a range of 0.1% to 5% (V/V). In some embodiments, said composition formed by mixing at least one bacteria and at least one fermenting microorganism increases ethanol production by a range of 0.1% to 10% (V/V). In some embodiments, said composition formed by mixing at least one bacteria and at least one fermenting microorganism increases ethanol production by a range of 0.1% to 20% (V/V). In some embodiments, said composition formed by mixing at least one bacteria and at least one fermenting microorganism increases ethanol production by a range of 2% to 5% (V/V). In some embodiments, said composition formed by mixing at least one bacteria and at least one fermenting microorganism increases ethanol production by a range of 5% to 10% (V/V). In some embodiments, said composition formed by mixing at least one bacteria and at least one fermenting microorganism increases ethanol production by a range of 5% to 20% (V/V). In some embodiments, said composition formed by mixing at least one bacteria and at least one fermenting microorganism increases ethanol production by a range of 10% to 20% (V/V).

In some embodiments, the at least one bacteria and at least one fermenting microorganism are packaged within a container. In some embodiments, the container is made of a material selected from the group consisting of thin-walled film or plastic (transparent or opaque), paperboard-based, foil, rigid plastic, metal (e.g., aluminum), glass, etc. In some embodiments, the content of the kit is packaged, as described below, to allow for storage of the components until they are needed. In some embodiments, some or all components of the kit may be packaged in suitable packaging to maintain sterility.

In some embodiments, the bacteria and the fermenting microorganism are stored in separate containers within the main kit containment element e.g., box or analogous structure, may or may not be an airtight container, e.g., to further preserve the sterility of some or all of the components of the kit.

In some embodiments, the dosage amount of the one or more bacteria and one or more fermenting microorganism provided in a kit may be sufficient for a single application or for multiple applications.

In those embodiments, the kit may have multiple dosage amounts of the one or more bacteria and one or more fermenting microorganism packaged in a single container, e.g., a single tube, bottle, vial, Eppendorf and the like.

In some embodiments, the kit may have multiple dosage amounts of the one or more bacteria and one or more fermenting microorganism individually packaged such that certain kits may have more than one container of one or more bacteria and one or more fermenting microorganism.

In some embodiments, multiple dosage amounts of the one or more bacteria and one or more fermenting microorganism may be packed in single separate containers.

In some embodiments, the kit contains instructions for preparing the composition used therein and for how to practice the methods of the invention.

In some embodiments, the kit further comprises a measuring utensil such as measuring spoon or a measuring cup.

In some embodiments, the instructions may be recorded on a suitable recording medium or substrate. For example, the instructions may be printed on a substrate, such as paper or plastic, etc.

In some embodiments, the instructions may be present in the kit as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In some embodiments, the bacteria used under the composition and/or the method of the invention is an isolated bacterium. In some embodiments, a biologically pure culture is also referred to as "an isolate". The term "isolate" is intended to specifically refer to an organism that is removed from its original source and purified from additional components with which it was originally associated, and thus is altered by the hand of man from its natural environment. It should be noted that the composition may include whole bacterial cells, parts thereof and extracts therefrom. Isolated bacterium refers to a bacterium that is e.g., cultivated, purified and/or cultured separately from the environment in which it is naturally located. Isolated material further encompasses bacterium isolated and cultured separately from the environment in which it was located, where these isolates are present in purified compositions that do not contain any significant amount of other microorganisms such as other bacterial strains. An "isolated bacterium" as used herein does not include the bacterium as it exists in its natural environment prior to isolation and/or substantial purification.

In some embodiments, the present invention further provides compositions and methods comprising variants and analogs of the disclosed bacterium. The term "variant" of a reference bacterium designates bacterium having variation(s) in the genomic sequence and/or polypeptide(s) encoded thereby as compared to the reference bacterium, while retaining the same phenotypic characteristic as the reference bacterium. Variants also encompass bacterium having variation(s) in the genomic sequence and/or polypeptide(s) encoded thereby as compared to the reference bacterium, while improving the phenotypic characteristic (e.g., secretion of any one of amylase, protease and cellulase, and combinations thereof) as the reference bacterium.

In some embodiments, the variants of the invention are genetically engineered variants (e.g., a result of genetically engineered mutation(s) to the nucleic acid sequence of the reference bacterium). The term "phenotypic characteristic" designates the morphology and/or host-range of a bacterium. Methods for phenotyping bacterium are well known in the art.

In some embodiments, the bacteria used under the composition and/or the method of the invention is a recombinant bacterium. Recombinant bacteria proteins be created artificially by recombinant DNA technology for use in the fermentation methods described herein. As used herein, a "recombinant nucleic acid" is a molecule where the nucleic acid molecule which encodes a polypeptide of interest has been modified in vitro, so that its sequence is not naturally occurring, or corresponds to naturally occurring sequences that are not positioned as they would be positioned in a genome which has not been modified.

In some embodiments, the bacteria used under the composition and/or the method of the invention comprises a recombinant nucleic acid encoding a hydrolase (e.g., any one of an amylase, a protease and cellulase), such as fused to a signal peptide.

The term "signal peptide" (or interchangeably "secretion peptide") is defined herein as an amino acid sequence typically present at the N-terminal end of newly synthesized secretory or membrane polypeptides which directs the polypeptide across or into a cell membrane of the cell (e.g., the plasma membrane in prokaryotes). As such, a signal peptide includes peptides, polypeptides and proteins that, when fused to a protein moiety form a chimeric protein that is secreted more effectively by a host cell as compared to the secretion of the same protein moiety alone. In some embodiments, the signal peptide of the present invention is capable of directing the hydrolase to a cell's secretory pathway. In some embodiments, the signal peptide of the present invention is capable of directing a hydrolase into or across a cell membrane. In some embodiments, the signal peptide of the present invention is capable of directing a hydrolase to the endoplasmic reticulum (ER), and into the membrane or the lumen of the ER.

Non-limiting examples of secretion peptides have been described by Antelmann H et. al, Genome Res. 2001 September; 11(9):1484-502, Wang G et. al., (Microb Cell Fact. 2015; 14(1):179), Bendtsen J D et. al., (BMC Microbiol. 2005 Oct. 7; 5:58) and Tjalsma H et. al., (Microbiol Mol Biol Rev. 2000 September; 64(3):515-47) and are selected from the group consisting of: Eno, PdhB, PdhD, YvgN, YwjH, CitH, RocA, RocF, Hagdual H, FlgKex, FliDex, KatAH, SodAH, YceD, Fus, Ef-G, GroEL, XepAex, XkdGex H, XkdKex, XkdMex, XlyAw ex, CwlCw ex, GapA, PdhA, albB, amyX, appB, estA, oppB, pbpX, phoD, qcrA, tlpA, wapA, wpra, adcB, yesM, yesW, yfkN, ykpC, ykuE, pghC, yubF, yuiC, tagV and efeB.

Other effective signal peptide coding regions for bacterial host cells may be obtained from the genes of *Bacillus* NCIB 11837 maltogenic amylase, *B. stearothermophilus* alpha-amylase, *B. licheniformis* subtilisin, *B. licheniformis* beta-lactamase, *B. stearothermophilus* neutral proteases (nprT, nprS, nprM) and *B. subtilis* prsS. Further signal peptides are described in Simonen and Palva (1993), Microbiological Reviews 57:109-137. Effective signal peptide coding regions for filamentous fungal host cells include but are not limited to the signal peptide coding regions obtained from *Aspergillus oryzae* TAKA amylase, *Aspergillus niger* neutral amylase, *Aspergillus niger* glucoamylase, *Rhizomucor miehei* asparatic proteinase, *Humicola insolens* cellulase and *Humicola lanuginosa* lipase. Variants of these signal peptides and other signal peptides are suitable, as well as expression mutants thereof having one or more silent mutations, as long as said signal peptide are effective in directing a polypeptide to and/or across the cell's membrane.

Additional, non-limiting examples of signal peptide are selected from the group of signal peptides that were described by Ulf Brockmeier (dissertation, 2006), said group consisting of: Epr, YncM, YjfA, YfhK, Csn, LytD, Bpr, WapA, BglC, LytB, LipA, YckD, Pel, YnfF, PhrK, YbdN, YobB, Yddt, YhfM, BglS, Vpr, AprE, YjdB, YbbE, PhrC, GlpQ, SacC, Yurl, PhoB, PenP, YfkD, YvpA, YdjM, AbnA, YwjE, YqgA, LipB, FliZ, DacB, SacB, YrvJ, YlaE, Pbp, Ybxl, YolA, Yqxl, YoaW, NprB, YlxF, YbfO, YlqB, SpoIIID, YwmC, YvbX, YkvV, YlxY, XynA, SleB, YbbC, YxiT, LytC, PhrA, YkvT, CotC, AmyE, NprE, YolC, YqzG, YndA, Yfj S, YvcE, YkwD, Mdr, YwfM, NucB, YqxM, YkoJ, Mpr, YpuA, TasA, YwmD, YwtD, YdbK, YfkN, YwaD, YpjP, RpmG, DacF, TyrA, LytF, WprA, YbbR, YhjA, YjiA, PbpD, YjcM, YhaK, PelB, SpoIIQ, MotB, YdhT, YbdG, LytE, PhrF, YhcR, CccA, CitH, AspB, YknX, YhdC, YlbL, YlxW, YngK, YnzA, YobV, YocH, YodV, YojL, YomL, YoqH, YoqM, YpbG, YpcP, YpmS, YpuD, YqzC, YraJ, YuaB, YusW, YvgO, YvgV, YvnB, YvpB, Ywcl, YwdK, YweA, YwgB, YwmB, YwoF, YwqC, YwsB, YwtC, YwtF, YxaK, YxiA, YybN and YycP.

In some embodiments, the signal peptide is operably linked to the N-terminus of the hydrolase. In another embodiment, the signal peptide is fused to the C-terminus of the hydrolase.

The term "operably linked" is intended to mean that the nucleotide sequence or amino acid sequence of interest is linked to the signal peptide (or nucleic acid sequence encoding the signal peptid) in a manner that allows for expression and secretion of the nucleotide or amino acid sequence (e.g. in an in vitro transcription/translation system or in a host cell when the vector or polypeptide is introduced into the host cell).

Definitions

As used herein the term "hydrolase" refers to enzymes that catalyze a hydrolysis reaction. Thus, hydrolases act to break down a compound (i.e., the substrate) by cleaving a covalent bond in the compound and inserting a water molecule across the bond. The general class of hydrolase enzymes includes those that act on ester bonds, on carbon-nitrogen bonds, on peptide bonds, on glycoside bonds, on ether bonds, and on acid anhydrides, among others.

As used herein the term "protease" refers to an enzyme that catalyzes the hydrolytic breakdown of proteins via hydrolysis of peptide bonds in a protein.

As used herein, the term "amylase" refers to an enzyme that is inter alia capable of catalyzing the degradation of starch. In particular they are hydrolases which are capable of cleaving α-D-(1→4) or α-D-(1→6) O-glycosidic linkages in starch.

As used herein the term "starch" refers to any material comprised of the complex polysaccharide carbohydrates of plants, comprised of amylose and amylopectin with the formula (C6H10O5)x, wherein x can be any number.

As used herein, the term "cellulose" refers to a polysaccharide consisting of a linear chain of several hundred to over ten thousand β(1,4) linked D-glucose units. Cellulose as used herein further refers to any source of cellulosic and/or lignocellosic/hemicellulosic biomass.

As used herein the term "polysaccharide" refers to a polymeric carbohydrate having a plurality of repeating units comprised of simple sugars. The term "polymeric" or "polymer" is meant to include both oligomeric and polymeric units and, preferably, those polysaccharides having more than four repeating monomeric simple sugar units.

As used herein, the term "antimicrobial" refers to the microbicidal or microbistatic properties of a compound, composition, article, or material that enables it to kill, destroy, inactivate, or neutralize a microorganism; or to prevent or reduce the growth, ability to survive, or propagation of a microorganism.

As used herein, the term "antimicrobial activity" refers to the ability of a compound to inhibit or irreversibly prevent the growth of a microorganism. Such inhibition or prevention can be through a microbicidal action, microbistatic inhibition or outcompeting bacteria by niche occupation.

The term "lysis" as used herein refers to the rupturing of a cell membranes or cell wall and release of the cytoplasm from the cell. As used herein, the term "lysate" refers to the material produced by the destructive process of lysis.

As used herein, the term "microorganism" refers to any organism or combination of organisms such as bacteria, viruses, protozoa, yeasts, fungi, molds, or spores formed by any of these.

As used herein, the term "fermenting microorganism" refers to a microorganism which can convert a fermentable carbon substrate to alcohol.

As used herein, the term "yeast" refers to eukaryotic microorganisms classified in the kingdom Fungi, having a cell wall, cell membrane and intracellular components. Yeasts are unicellular, although some species become multicellular through the formation of a string of connected budding cells known as pseudohyphae, or false hyphae.

As used herein, the term "yeast" refers to microorganisms capable of living and growing in either aerobic (with oxygen), anaerobic (lacking oxygen) or microaerophilic (with low levels of oxygen) environments.

As used herein, the term "fermentable carbon source" or "fermentable carbon substrate" or "fermentable material" refers to a carbon source capable of being metabolized by the microorganisms disclosed herein for the production of fermentative alcohol. Suitable fermentable carbon sources include, but are not limited to, monosaccharides such as glucose, galactose (because it can be released from hemicellulose) or fructose; disaccharides such as maltose, lactose or sucrose; oligosaccharides; polysaccharides such as starch or cellulose; C5 sugars such as xylose and arabinose; one carbon substrates including methane; and mixtures thereof.

As used herein, the term "product alcohol" or "alcohol" refers to any alcohol that may be produced by a microorganism in a fermentation process that utilizes biomass as a fermentable carbon source. Product alcohols include, but are not limited to, C1 to C8 alkyl alcohols. In some embodiments, the product alcohols are C2 to C8 alkyl alcohols. In other embodiments, the product alcohols are C2 to C5 alkyl alcohols. It will be appreciated that C1 to C8 alkyl alcohols include, but are not limited to, methanol, ethanol, propanol, butanol, pentanol, and isomers thereof. Likewise, C2 to C8 alkyl alcohols include, but are not limited to, ethanol, propanol, butanol, pentanol, and isomers thereof "Butanol" as used herein refers to butanol isomers: 1-butanol (1-BuOH), 2-butanol (2-BuOH), tertiary-butanol (tert-BuOH), and/or isobutanol (iBuOH, i-BuOH, or I-BUOH), either individually or as mixtures thereof.

"Propanol" as used herein refers to the propanol isomers: isopropanol or 1-propanol.

"Pentanol" as used herein refers to the pentanol isomers: 1-pentanol, 3-methyl-1-butanol, 2-methyl-1-butanol, 2,2-dimethyl-1-propanol, 3-pentanol, 2-pentanol, 3-methyl-2-butanol, or 2-methyl-2-butanol.

As used herein, the term "bioethanol" refers to ethanol produced partially or entirely from biomass. In certain embodiments, bioethanol is produced by fermentation of sugars derived from biomass. The term bioethanol is used interchangeably herein with the term ethanol.

As used herein, the term "biomass" refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers and animal manure, sugarcane and sugar beet molasses, sugarcane juice.

In some embodiments, the composition and method of the present invention increases nutritive value of dried distillers' grains (e.g., DDG) used for animal feeding.

As used herein, the term "fermentation of sugars" or "fermentable sugar" refers to one or more sugars and/or sugar derivatives (including monomers, dimers, and polymers of these compounds including two or more of these compounds) capable of being metabolized by the microorganisms disclosed herein for the production of fermentative alcohol. In some cases, the organism may break down these polymers, such as by hydrolysis, prior to incorporating the broken-down material. Exemplary fermentable sugars include, but are not limited to glucose, xylose, arabinose, galactose, mannose, rhamnose, cellobiose, lactose, sucrose, maltose, and fructose.

As used herein, "sugar" refers to oligosaccharides, disaccharides, monosaccharides, and/or mixtures thereof. The term "saccharide" also includes carbohydrates including starches, dextrans, glycogens, cellulose, pentosans, as well as sugars.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Microbial Isolations

Bacterial isolations were performed out of American Yellow corn No. 2, several animal-feed corn products (Amir Dagan mixture institute, Haifa, Israel), biopesticides, Natto bacillus strains isolated from commercial Natto food products and from different bacterial collections. Enrichment of animal-feed products was established with saline suspension and incubation at 32.5° C. for 24 hr. Isolates originated from corn fermentations were obtained from samples taken at different time points, starting in unfermented corn.

In addition, bacterial isolations were conducted from chicken feathers (Ha'Yogev, Israel). Feathers were transferred to a Brain-Heart infusion broth (BD Brain Heart Infusion, Difco), and incubate in aerobic conditions. Sporulation was induced through nutrient starvation, and spores were selected following an 80° C. heat-shock of 20 minutes in a water bath.

Cultures were preserved at −80° C. in Cryoprotective Solution of 25% (v/v) Glycerol and 50% (v/v) LB (1% tryptone, 0.5% yeast extract, 1% NaCl).

Phenotypic Characterization

Starch digestion. Isolates were inoculated onto starch agar plates (2% soluble corn starch, 0.5% Bacto-peptone, 0.3% beef extract, and 2% agar). The plates were incubated for 2 days at 32.5° C. followed by 5 days at RT, and flooded with Lugol's Iodine, to observe the appearance of a clear halo (FIG. 1).

Starch degradation kinetics. Isolates were inoculated into 3 ml LB, and incubation at 32.5° C. for 4 hours to mid logarithmic growth phase. The bacteria were then diluted 1:100 in 150 µl LB and in LB enriched with 2% soluble corn starch in 96-well microplate, and incubated for 24 hours at 32° C. in a microaerophilic environment with orbital agitation in a microplate reader (Synergy HT, BioTek, USA). Optical density was measured every 2 minutes at 600 nm. Tests were done in three technical repeats.

Figure 2A:
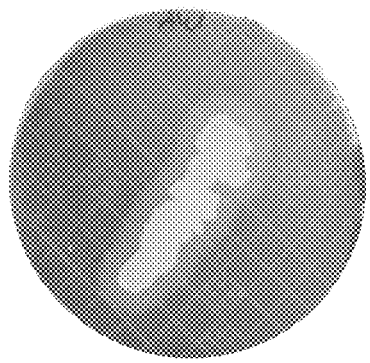
FIGS. 2A-B Present agar plates where gelatinase activity test was performed. Isolate AU1 presents positive activity (FIG. 2A) and isolate NN1 Presents negative activity and a pH reduction seen as yellowing of the agar (FIG. 2B). Plates were incubated at 32.5° C. and reviewed after 24 and 48 hours.
Figure 2B:
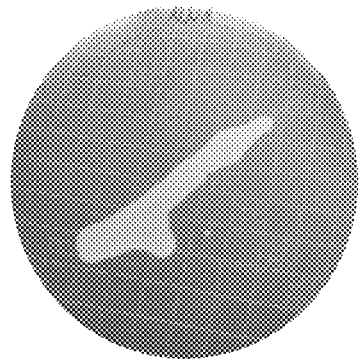

Gelatinase activity. (Proteolytic activity indication) Activity was assessed through inoculation of strains in gelatin agar plates (3% gelatin, 1% casein enzymatic hydrolysate, 2% agar, and 0.02% Congo red at pH 7.2). Gelatinase activity was identified when a clearing zone of protein degradation was present following 24 and 48 hours of incubation at 32.5° C. (FIGS. 2A-B).

Antimicrobial activity determination. Activity was determined against two strains: Gram-positive *Listeria innocua* ATCC 33090 and Gram-negative *Escherichia coli* ATCC 8739. Isolates were incubated in LB for 4 hours at 32.5° C., then 3 and 5 µl suspension was spotted on LA plates preinoculated with $10^5$ CFU of *L. innocua* or *E. coli*, respectively. Plates were incubated overnight at 37° C., and inhibition zones diameters were measured.

Starch Utilization Evolution

Four strains (strain 4, strain 8, *B. subtilis* ATCC 6633, and *B. cereus* ATCC 11788) were incubated in starch agar plates for 2 days at 32.5° C. followed by 5 days at RT. Strains were then re-cultured in fresh starch plates, and underwent the same incubation period. Plates were examined for improved starch degradation (FIG. 1) and improved bacterial growth rate (see above).

Genomic Identification of Isolates

Microbial DNA was extracted and purified using DNeasy Blood & Tissue (Qiagen, Hilden, Germany). Sanger sequencing of the 16s rDNA, DNA gyrase beta subunit (gyrB), and RNA polymerase beta subunit (rpoB) genes was carried out, following by results analysis using Sequencing Analysis and SeqScape software (Applied Biosystems). The obtained sequences were compared to all available genomes at the GenBank database, using the BLASTn algorithm hosted by the National Center for Biotechnology Information, Bethesda, USA.

Bacterial Growth Under Ethanol Stress

Isolates were tested for their ability to tolerate ethanol stress similarly to the stress occur following the initial 24 hours of corn ethanol fermentations. Single bacterial colonies were inoculated into 3 ml LB, and incubation at 32.5° C. for 4 hours to mid logarithmic growth phase. Next, the bacteria were diluted 1:100 in 150 µl Brain-Heart Infusion (Difco) and were exposed to 0-10% (v/v) ethanol with starting absorbance of $0.1 OD_{600\,nm}$, in a 96-well microplate, and incubated for 24 hours at 32° C. in a microaerophilic environment with orbital agitation in a microplate reader (Synergy HT, BioTek, USA).

Corn Mash Preparation

32% (w/v) American Yellow corn No. 2 were added to tap water at pH of 5.2-5.6, and were hydrolyzed with 0.0255% (v/v) Avantec Amp (Novozymes) at 80° C. for 200 min. The mash was then cooled at RT for 2 hours, and tested for initial glucose concentration using enzymatic glucose assay kit (GAHK, Sigma Aldrich). 0.072% (w/v) urea was added.

Ethanol Production

*S. cerevisiae* commercial strains Eagle C6 Fuel (Lallemand Biofuels & Distilled Spirits), Ethanol Red (Lesaffrea), and Kol-Excel-3 (Kol Capital) were used as ethanol producing yeast. Yeast strains were grown on Yeast Extract Peptone Dextrose (YPD) medium (2% Bacto-peptone, 2% glucose, 1% Bacto-Yeast Extract) at 30° C. overnight.

Isolated bacteria were deliberately added to yeast fermentation to determine the bacterial effect on pH levels, glucose consumption, starch hydrolysis, other bacterial contaminants, and ethanol production. Bacteria were inoculated into 3 ml LB, and incubation at 32.5° C. for 4 hours, ranging in density of $10^4$-$10^{10}$ CFU/ml.

Deliberate inoculation of corn fermentation was assessed by mimicking industrial corn fermentation on a small scale. When used, 0.5 ppm Penicillin (Bactenix V60, Lallemand Biofuels & Distilled Spirits), and 10 ppm Virginiamycin (Lactrol, PhibroChem) were added. Fermentations were conducted in biological duplicates on different days at 32.5° C., 160 RPM, for 50 hours, in a microaerophilic environment. Ethanol quantification was done in three time points, 17-19, 41, and 50 hours, in 2 technical replications, using Gas Chromatograph (GC) with FID detector (Trace 1300, Thermo Fischer Scientific). pH was determined using litmus paper.

Fermentations were carried out in the absence or in the presence of isolated bacteria to determine the bacterial effect on pH levels of the fermentation, glucose consumption, starch hydrolysis, other bacterial contaminants, and ethanol production. Bacteria were inoculated into 3 ml LB, and incubation at 32.5° C. for 4 hours, ranging in density of $10^4$-$10^{10}$ CFU/ml.

Example 1

Microbial Isolations

Following the biofuel industry demand list, the inventors desired to find bacteria that are fast growers, produce amylase and protease, don't acidify the mash, have antibacterial properties but are not antifungal, and will be inhibited and lysed when exposed to high ethanol concentrations.

Over several courses of enrichment and isolation, over 200 strains were isolated from corn and animal-feed corn products. Less than half were determined as non-pathogenic according to genomic data. In addition, "Natto" fermented food product were also subjected to bacterial isolation, as a source of potentially non-pathogenic *Bacillus* strains with amylolytic ability and other abilities. Isolations from biopesticide should contain strains which are certificated for agriculture use.

*Bacillus* was the dominating genus in all isolations: *B. badius, B. velezensis, B. invictae/pumilus, B. subtilis*, and *B. thuringiensis* were all identified during the isolations. In addition, *Pseudomonas putida, Paenibacillus cookii*, and *P. chitinolyticus* were also isolated among the non-pathogenic bacteria.

The *Bacillus* genus includes some strains able to produce defense molecules and extracellular enzymes. While they are aerobic or facultative, their endospores form only under aerobic conditions, and are highly resistant to chemical and physical agents Also, it is possible to completely eliminate sporulation of these strains by introducing mutations in genes responsible for sporulation. Non-limiting examples of suitable mutations may be found in Masel et al. 2017 (Genetics 175:453-457); Grossman et al. 1992, (Biochimie 74, 679-688); Widderich et al. 2016, Mol Microbiol 100(1):108-124; Higgins and Dworkin 2012 (FEMS Microbiol Rev, 36(1):131-148) and Quisel and Grossman, 2000 (Journal od Bacteriology 3446-3451). This will prevent spore formation that could be problematic in terms of losing organic materials that can be otherwise lysed and used by the yeast as a nutrition source during fermentation. Absolut elimination of spores is further important as spores are highly resistant to high temperature and cleaning agents between fermentation batches.

Among *Bacillus* secreted enzymes utilized in industrial processes, stands the alpha-amylase enzyme. Glucoamylase is also secreted by some *Bacillus* species. When grown anaerobically in a medium supplemented with glucose, *B. subtilis* produces lactate, acetate, and 2,3-butanediol.

Example 2

Starch Utilization Evolution

Figure 3:
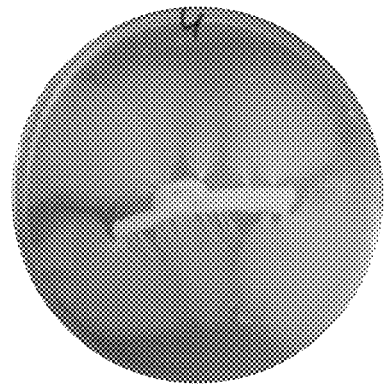
FIG. 3 Presents the altered morphology of isolate 4 on starch agar plate.

Strains were tested in starch agar plate for evolved and enhanced starch degradation. Isolate 4 presented altered morphology (an outcome of spontaneous mutations), and 14 new isolates were selected from its colonies (FIG. 3). The new isolates were tested for starch degradation in agar and liquid, and the rankings are described below (Tables 1 and 2). While the parental strain (isolate 4) didn't possess starch degradation, three strains of the 14 presented improved starch degradation.

Example 3

Starch Degradation

Figure 4:
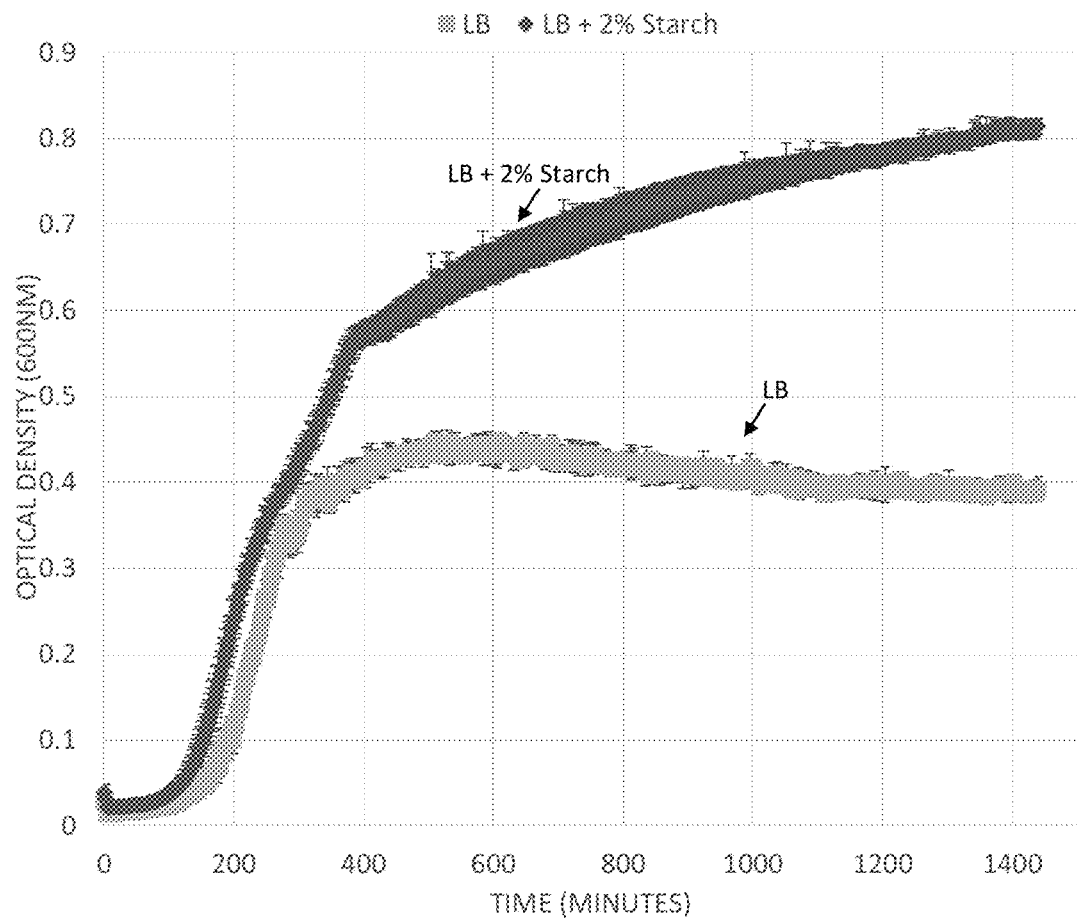
FIG. 4 Presents a graph with growth kinetics curves of isolate CN1 in LB and LB supplemented with 2% starch.

Starch degradation kinetics in liquid medium was assessed on LB supplemented with 2% starch vs. LB representing the baseline. Example of starch degradation kinetics of isolate CN1 (*B. thuringiensis/cereus*) is shown in FIG. 4. Starch degradation was further assessed in agar plates, detected by the presence of a halo under iodine exposure. The two degradation assays demonstrated a good correlation. Isolate CN1, for instance, which starch degradation results in liquid medium are demonstrated in FIG. 4, indeed displayed a clearing zone surrounding its colony on starch agar plate. Activity of amylases in *B. thuringiensis* as well as in *B. cereus* has been previously described numerous times.

The 73 tested strains were ranked on a scale of 1 to 5 for starch degradation ability, in a combined rank determined from starch agar plates and liquid starch broth (Table 1).

TABLE 1

Starch degradation ranking in a scale of 1 to 5.

| Isolate | Rank | Isolate | Rank |
|---|---|---|---|
| 4 | 0 | *B. subtilis* ATCC 6633 | 4 |
| 4-1 | 0 | LHS | 1 |
| 4-2 | 0 | LHS-N | 1 |
| 4-3 | 0 | LHN1 | 0 |
| 4-4 | 0 | LHN2 | 0 |
| 4-5 | 0 | LHN2-1 | 0 |
| 4-6 | 0 | BV1 | 0 |
| 4-7 | 0 | BV2 | 0 |
| 4-8 | 0 | BV3 | 0 |
| 4-9 | 3 | BV4-1 | 0 |
| 4-10 | 0 | BV4-2 | 0 |
| 4-11 | 0 | NCN1 | 0 |
| 4-12 | 2 | NCN2 | 0 |
| 4-13 | 1 | NCN3 | 0 |
| 4-14 | 0 | NCN4 | 0 |
| 8 | 5 | NCN4-2 | 0 |
| CA2 | 3 | NCS1 | 1 |
| NN1 | 0 | NCS2 | 1 |
| NN4 | 0 | NCS3 | 1 |
| CN1 | 3 | NCS4 | 1 |
| APH1 | 0 | NCN4-2 | 1 |
| APH2 | 0 | INCS1 | 1 |

TABLE 1-continued

Starch degradation ranking in a scale of 1 to 5.

| Isolate | Rank | Isolate | Rank |
|---|---|---|---|
| BL1 | 0 | INCS2 | 1 |
| BL2 | 1 | CAS1 | 2 |
| BL3 | 0 | CAS2 | 1 |
| SEF1 | 2 | CAS3 | 1 |
| SEF2 | 0 | CAS4 | 1 |
| CH1 | 0 | CAS5 | 0 |
| CH2 | 2 | ICAS | 1 |
| CH3 | 0 | ICAS2 | 1 |
| AB1 | 3 | GFS | 2 |
| AU1 | 1 | IGF | 1 |
| AU2 | 0 | ACN1 | 0 |
| F3 | 0 | ACN2 | 0 |
| SM3 | 1 | ACN3 | 0 |
| KLU1 | 2 | ACN4-2 | 0 |
| KLU3 | 1 | ACN5 | 0 |
| *B. cereus* ATCC 11778 | 3 | Natto | 1 |
| "Probit" pesticide | 3 | *Bacillus megatevioil* VS1 | 2 |
| *Bacillus simplex* SHB26 | 0 | *Bacillus amylaliquegaciens* F2B42 | 1 |
| *Serratia plymuthica* | 1 | *Bacillus atrophaeus* 1942 | 1 |
| *Bacillus thuringie-nsis* HD73 | 3 | *Bacillus pumilus* ATCC 70161 | 0 |
| *Bacillus ceveous* AH621 | 0 | *Bacillus toyonensis* | 3 |
| *Bacillus subtilis* 3610 | 0 | | |

Out of 73 isolates tested for amylase activity, 31 strains presented starch degradation and utilization (Table 1). The majority of the positive strains were identified as members of the *Bacillus* genus.

Example 4

Protease Activity

Corn used for ethanol production contains high percentage of protein. An average of 31% protein concentration is present in DDGS, hinting inefficient utilization of the nitrogen source by the industry. Proteolysis during fermentation will introduce essential nitrogen to the yeast, thus enhancing ethanol production. Many *Bacillus* strains are reported to produce robust proteases.

Strains were ranked on a scale of 1 to 5 for gelatin degradation ability (Table 2). pH lowering isolates received an additional ranking of "AP" (Acidic pH).

TABLE 2

Gelatin degradation ranking in a scale of 1 to 5, AP marking stands for pH reduction.

| Isolate | Rank | Isolate | Rank |
|---|---|---|---|
| 4 | 1 | BV1 | 0 |
| 4-9 | 1 | BV2 | 2 |
| 4-12 | 2 | BV3 | 1 |
| 8 | 2 | BV4-1 | 3 |
| CN1 | 2 | BV4-2 | 4 |
| CA2 | 5 | NCN1 | 4 |
| NN1 | 0(AP) | NCN2 | 0 |
| NN4 | 3 | NCN3 | 0 |
| APH1 | 0 | NCN4 | 0 |
| APH2 | 2 | NCS1 | 5 |
| BL1 | 1 | NCS2 | 1(AP) |
| BL2 | 2 | NCS3 | 1(AP) |
| BL3 | 1 | NCS4 | 0(AP) |
| SEF1 | 2 | NCN4-2 | 1(AP) |
| SEF2 | 0 | INCS1 | 0 |
| CH1 | 0 | INCS2 | 0 |
| CH2 | 1 | CAS1 | 2 |
| CH3 | 0 | CAS2 | 5 |
| AB1 | 1 | CAS3 | 0 |
| AU1 | 2 | CAS4 | 2 |
| AU2 | 2 | CAS5 | 0 |
| F3 | 0 | ICAS | 0(AP) |
| SM3 | 1 | ICAS2 | 3 |
| KLU1 | 0 | GFS | 2 |
| KLU3 | 1 | IGF | 1 |
| *B. cereus* ATCC 11778 | 3 | ACN1 | 0 |
| *B. subtilis* ATCC 6633 | 2 | ACN2 | 1 |
| LHS | 0 | ACN3 | 1 |
| LHS-N | 5 | ACN4-2 | 5 |
| LHN1 | 0 | ACN5 | 2 |
| LHN2 | 3 | IACS | 0 |
| LHN2-1 | 2 | Natto | 3 |
| "Probit" pesticide | 1 | *Bacillus megatevioil* VS1 | 3 |
| *Bacillus simplex* SHB26 | 1 | *Bacillus amylaliquegaciens* F2B42 | 3 |
| *Serratia plymuthica* | 3 | *Bacillus atrophaeus* 1942 | 3 |
| *Bacillus thuringie-nsis* HD73 | 1 | *Bacillus pumilus* ATCC 70161 | 3 |
| *Bacillus ceveous* AH621 | 3 | *Bacillus toyonensis* | 1 |
| *Bacillus subtilis* 3610 | 3 | | |

44 isolates were tested positive for gelatinase activity (Table 2). Six of them (marked as "AP") lowered the pH of the medium and therefore may not be suitable for the bioethanol industry.

Example 5

Bacterial Growth Under Ethanol Stress

Bacteria are exposed to increasing ethanol concentrations during production of corn ethanol. Ethanol concentrations reach about 17% (v/v) by the end of commercial fermentations, and bacterial isolates are expected to withstand only up to 7% ethanol. This ethanol sensitivity trait of the isolates can serve as a mean to control the presence and dose of the isolates in the fermentation. All isolates were exposed to increasing ethanol concentrations (see FIG. 5 for the performance of a representative isolate).

Growth rate under ethanol stress was determined for the bacterial isolates (Table 3).

TABLE 3

Growth rate under increasing ethanol concentration.

| | Growth Rate [1/min] | | | | |
|---|---|---|---|---|---|
| Isolate | 0% EtOH [v/v] | 2.5% EtOH [v/v] | 5% EtOH [v/v] | 7.5% EtOH [v/v] | 10% EtOH [v/v] |
| APH1 | 0.004983 | 0.003322 | 0.000997 | 0.000997 | 0.000997 |
| BL1 | 0.005647 | 0.003986 | 0.002325 | 0.001329 | 0.000997 |
| CH1 | 0.009634 | 0.006976 | 0.004319 | 0.002325 | 0.001329 |
| APH2 | 0.00764 | 0.004983 | 0.002658 | 0.001993 | 0.001661 |
| SM3 | 0.006312 | 0.003322 | 0.00299 | 0.002325 | 0.001661 |
| KLU1 | 0.008969 | 0.006312 | 0.003322 | 0.001661 | 0.001661 |
| CH2 | 0.008637 | 0.005979 | 0.003986 | 0.001993 | 0.001993 |
| BL2 | 0.007973 | 0.005315 | 0.003322 | 0.00299 | 0.002325 |
| F3 | 0.004983 | 0.003654 | 0.002325 | 0.001993 | 0.002325 |
| NN1 | 0.011959 | 0.009634 | 0.005315 | 0.003322 | 0.002658 |
| BL3 | 0.008305 | 0.004983 | 0.003654 | 0.002658 | 0.002658 |
| CH3 | 0.008969 | 0.006312 | 0.004983 | 0.00299 | 0.002658 |
| KLU3 | 0.009966 | 0.00764 | 0.004651 | 0.00299 | 0.002658 |
| *B. subtilis* ATCC 6633 | 0.010962 | 0.008305 | 0.004983 | 0.003654 | 0.002658 |
| 8 | 0.011295 | 0.008305 | 0.005315 | 0.003322 | 0.00299 |
| SEF2 | 0.01063 | 0.007973 | 0.005315 | 0.003654 | 0.00299 |
| CA2 | 0.012623 | 0.008637 | 0.005647 | 0.003986 | 0.003322 |
| NN4 | 0.011627 | 0.008969 | 0.004983 | 0.003322 | 0.003322 |
| SEF1 | 0.011295 | 0.008305 | 0.005979 | 0.003986 | 0.003322 |
| AB1 | 0.013952 | 0.008637 | 0.005647 | 0.003986 | 0.003322 |
| *B. cereus* ATCC 11778 | 0.011959 | 0.008969 | 0.006312 | 0.003654 | 0.003322 |
| 4 | 0.012291 | 0.008969 | 0.005979 | 0.003654 | 0.003654 |
| CN1 | 0.011627 | 0.009301 | 0.004983 | 0.004319 | 0.003654 |
| AU1 | 0.011295 | 0.008305 | 0.004651 | 0.003654 | 0.003654 |
| AU2 | 0.014616 | 0.009966 | 0.008637 | 0.006312 | 0.005647 |

The presented values are an average of six replicates.

Figure 5:
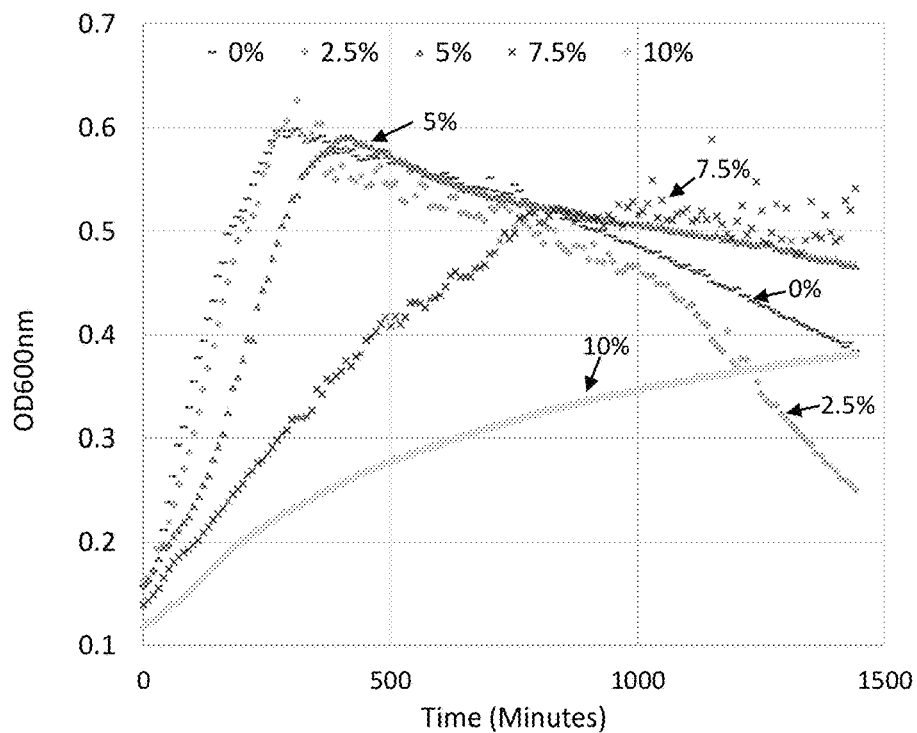
FIG. 5 Presents a graph with ethanol stress kinetics curves of isolate 4 (*B. invictae/pumilus*).

As expected and desired, for all isolates tested, the higher the ethanol, the slower the growth rate (Table 3). The isolates are differently affected by ethanol stress at different ethanol titers, enabling to choose and design the desired activity duration of the bacterium in a customized manner. Isolate 4, identified as *B. invictae/pumilus*, exhibited good growth rate up to 7.5% v/v of ethanol, following a decrease in turbidity that could be attributed to cell death and lysis (FIG. 5 and Table 3). This may insure that the beneficial contribution of the bacterium may last up to approximately 20 fermentation hours, but no longer, and that the cell lysate of the bacterium may be used by the yeast as additional nutritional source.

Example 6

Antimicrobial Activity 73 strains were tested for their antibacterial activity against *E. coli* and *L. innocua*, representing Gram negative and Gram-positive bacterial contaminants respectively, however only one isolate presented antibacterial activity. This strain, isolate 8, was able to inhibit the growth of *L. innocua*. It is however important to note that bacterial inhibition is not the only mechanism results in inhibition of contaminating bacteria. Other mechanisms for inhibition of contaminating bacteria may include outcompeting the contaminants by increased growth rate of the beneficial bacteria due to better utilization of available nutrients. In order to assess the presence of inhibiting effect of our isolates on contaminating bacteria, 73 isolates from our collection were co-cultured with the strains *L. gasseri* and *L. casei* representing potential contaminants belonging to the group of lactic acid bacteria (LAB), the most common contaminants. All *Bacillus* strains presented much higher growth rates than both LAB strains. Therefore, prevention of LAB development has been achieved (data not shown).

Example 7

Corn Ethanol Production

Industrial corn ethanol production protocol was mimicked in lab conditions, i.e., corn mash fermentation in a Simultaneous Saccharification and Fermentation (SSF) process. All fermentations included a commercial ethanol producing yeast strain.

Figure 6A:
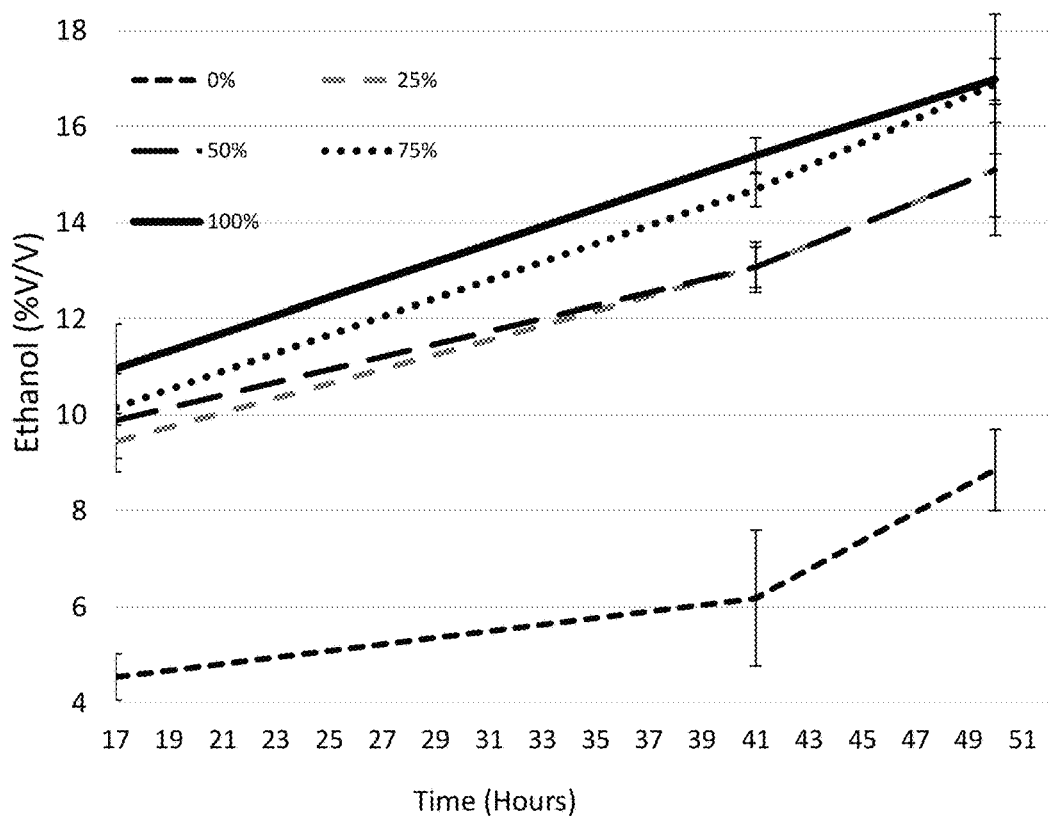
FIGS. 6A-B Present graphs with ethanol production by Eagle C6 Fuel in 32% corn mash. Effect of increasing glucoamylase concentration (FIG. 6A) and effect of increasing antibiotic concentration (FIG. 6B).
Figure 6B:
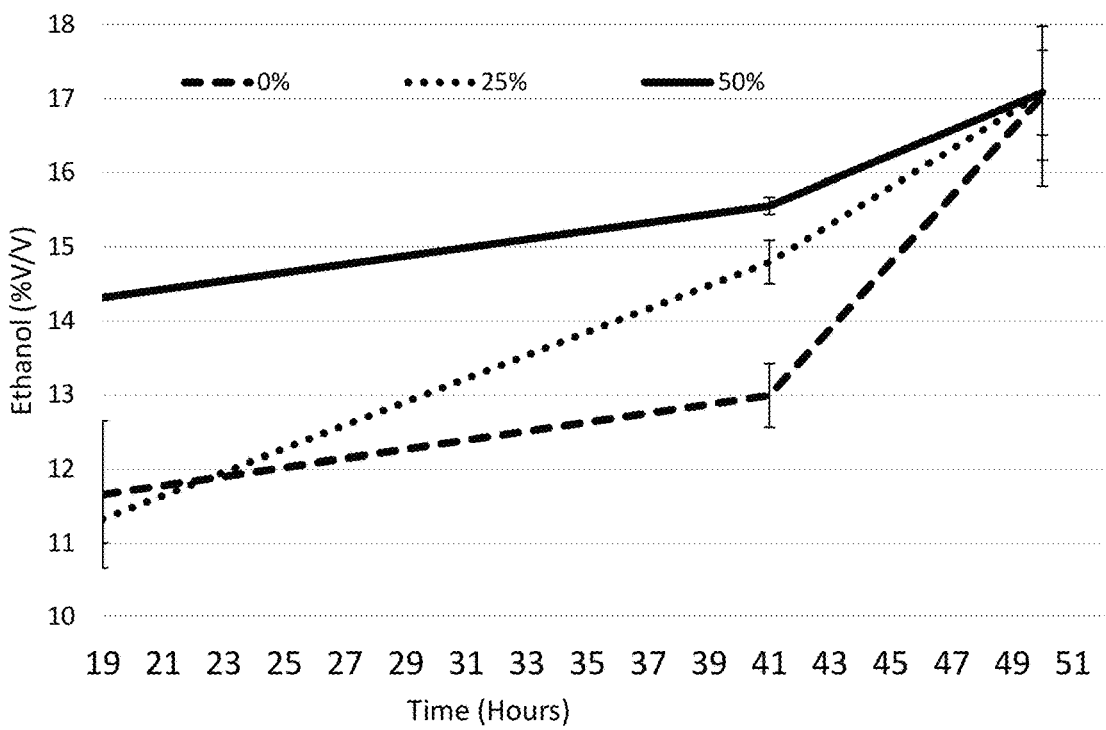

The effect of the addition of the isolated bacteria, glucoamylase, and antibiotics concentration on ethanol production as a function of time using a commercial yeast strain Eagle C6 Fuel was determined (FIG. 6A-B).

Extraneous glucoamylase contributed greatly to ethanol production (FIG. 6A-B), however only slight reductions were found when comparing 75% and 100% of industrial glucoamylase concentration. Antibiotic concentration was found to be linked to fermentation rate, as the final ethanol concentration was similar in all three antibiotics concentrations.

Example 8

Bacterial Concentration

Prior to assessing the beneficial effect of our bacterial isolates in ethanol fermentations, the appropriate range of bacterial concentrations to be added to fermentations was determined. Bacterial concentration should be crucial as it may either enhance or deter ethanol production. Too much bacteria may dominate the fermentation and use nutritional resources necessary for yeast. Small amounts of bacteria could have little to no effect in terms of enzymes production and secretion of antibacterial defense molecules or outcompeting harmful bacteria.

Figure 7:
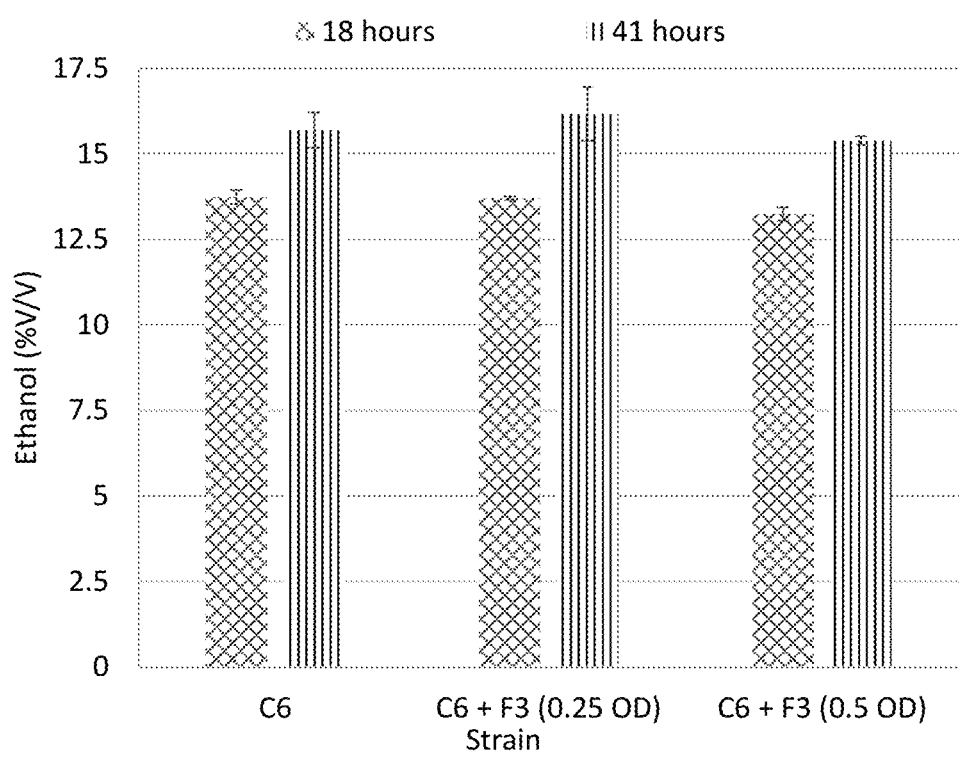
FIG. 7 Presents a bar graph with the Ethanol concentration determined during corn fermentation of commercial yeast strain Eagle C6 Fuel and bacterial isolate F3 (genetically similar to *Bacillus* sp. RS(2010)).

Bacterial isolates were added to yeast fermentations in varied optical densities. While the addition of $0.25 OD_{600\,nm}$ of isolate F3 had slight but apparent improvement in total ethanol production, an increase to $0.5 OD_{600\,nm}$ was found to be damaging (FIG. 7). Therefore, a bacterial concentration of $0.25\ OD_{600}$ was adopted for the next experiment (see below).

Optimal bacterial concentration was assessed by deliberate inoculation of corn fermentation with 0.5 ppm Penicillin, 10 ppm Virginiamycin, 0.065% (v/v) glucoamylase, and 0.072% (w/v) urea. Fermentations were conducted in biological duplicates at 32.5° C., 160 RPM, for 50 hours, in a microaerophilic environment.

Example 9

Assessment of Ethanol Production Ability with Beneficial Bacterial Isolate Under Glucoamylase and Antibiotic Reduction A mix of bacterial strains originating in commercial American corn ethanol facility (Pinal energy, AZ, USA) was added to induce massive contamination and pH reduction, and to review the ability of the isolated strains. The mix served as bacterial representation of damaging bacteria from the ethanol industry. In addition, each fermentation was supplemented with one bacterial isolate, as a method to examine the ability of each isolate. *B. cereus* ATCC 11778 and *B. subtilis* ATCC 6633 acted as controls. The fermentations were conducted with no antibiotics and glucoamylase. Small amount of 0.065% (v/v) glucoamylase was used during corn digestion (FIG. 8A-B).

The beneficial abilities of our isolates were evaluated under reduction of glucoamylase and no antibiotics, while deliberately inoculating fermentations with harmful bacteria. Fermentations were supplemented with one bacterial isolate at a time, to uncover the effect of each isolate. As most of the tested isolates belonged to the genus *Bacillus*, *B. cereus* ATCC 11778 and *B. subtilis* ATCC 6633 served as controls.

Bacterial impact on ethanol production was determined under deliberate inoculation of digested corn fermentation with no antibiotics, and no glucoamylase, and 0.072% (w/v) urea. Fermentations were conducted in biological duplicates at 32.5° C., 160 RPM, for 50 hours, in a microaerophilic environment.

Figure 8A:
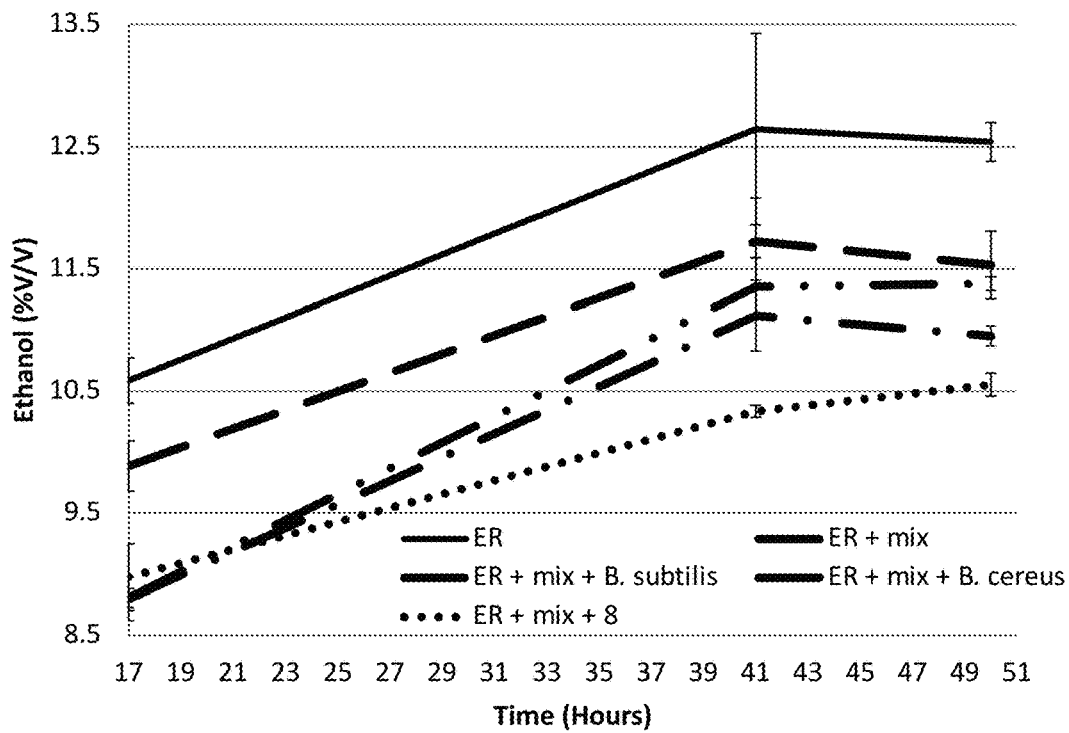
FIGS. 8A-B Present graphs with ethanol production by commercial yeast strain Ethanol Red under a mix of bacterial contaminants and selected isolates. Graphs A and B represent two fermentation conducted in two biological replicates with different tested bacterial strains.
Figure 8B:
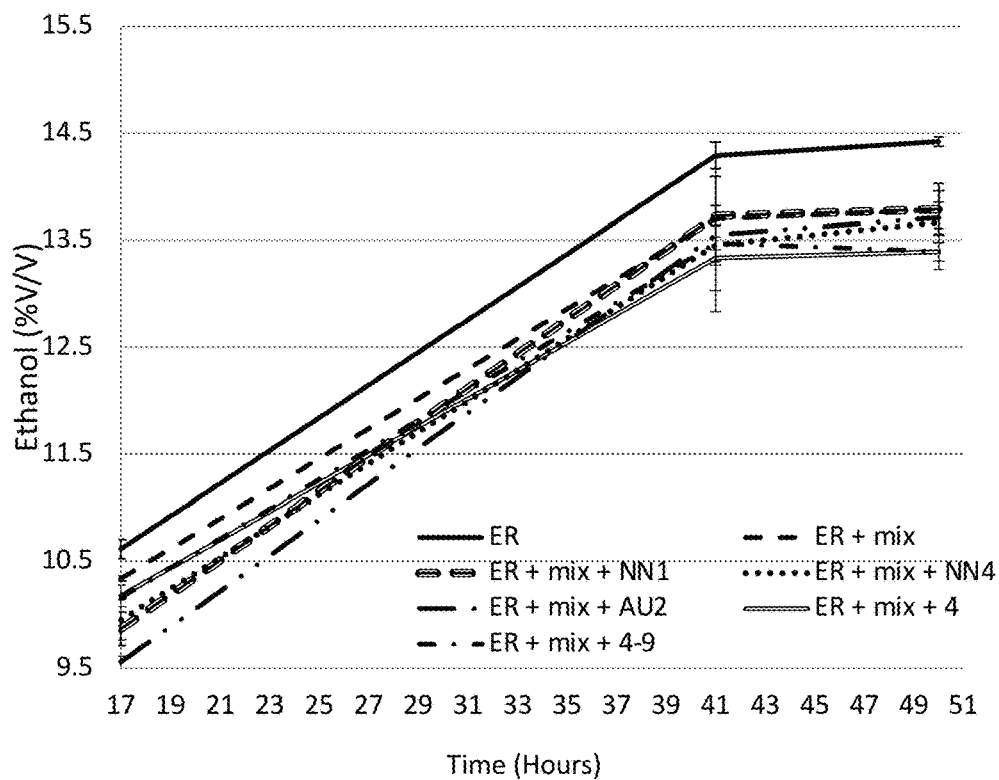

Ethanol production was reduced greatly as response to bacterial contamination, consistently in all experiments (FIGS. 8A, 8B, 9A, 9B). The addition of the ATCC control strains further deteriorated the ethanol production as contributed to a farther decrease in ethanol concentration during all fermentation time-points. In the experiments presented at FIGS. 8A-B and 9A-B neither of the tested isolates, namely isolate 8 (*B. subtilis*), NN1 (*P. putida*), NN4 (*B. thuringiensis*), AU2 (*B. badius*), 4 (*B. invictae/pumilus*), and 4-9 (offspring of strain 4), succeeded to correct the damage done by the induced contamination or by the reduction of glucoamylase (FIGS. 8A-B).

Figure 9A:
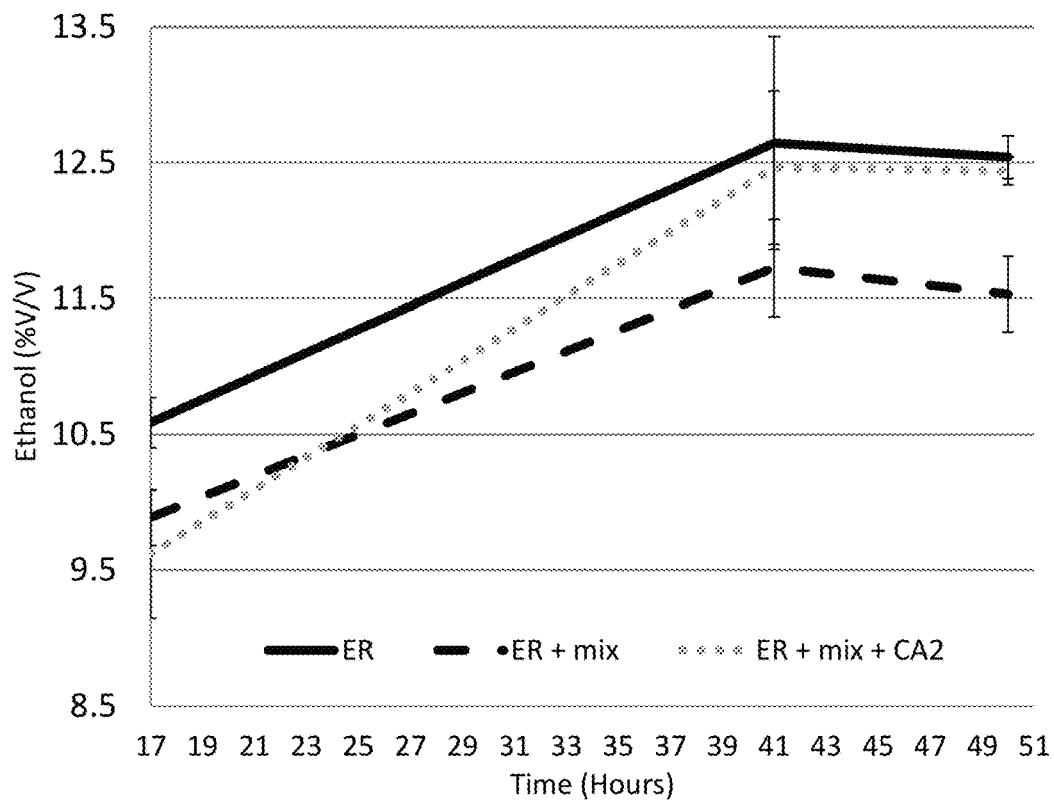
FIGS. 9A-B present graphs with Ethanol production by commercial yeast strain Ethanol Red under a mix of bacterial contaminants and isolate CA2. Graphs A and B represent two fermentation conducted in two biological replicates.
Figure 9B:
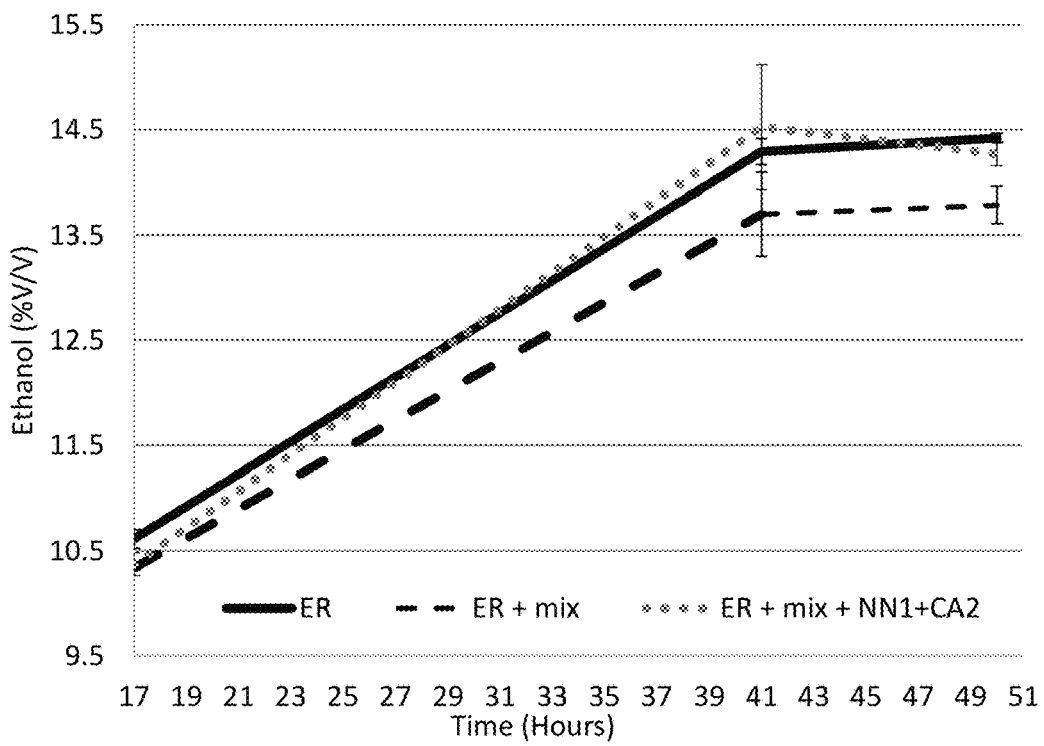

On the contrary, isolate CA2 was observed to have positive contribution to ethanol production (FIG. 9A-B). Isolate CA2 (*B. thuringiensis*) increased ethanol production, either by outcompeting the harmful bacteria or through its amylolytic ability that meets the glucoamylase challenge. Isolate CA2 was found to have proteolytic and amylolytic abilities with no pH reduction. The inventors tried to further improve ethanol productivity by adding another strain (isolate NN1). The two-strain mixture found to result in comparable results to those of isolate CA2 alone (FIGS. 9A-B).

Bacterial impact on ethanol production was determined under deliberate inoculation of digested corn fermentation with no antibiotics, no glucoamylase, and 0.072% (w/v) urea. Fermentations were conducted in biological duplicates at 32.5° C., 160 RPM, for 50 hours, in a microaerophilic environment.

Figure 10:
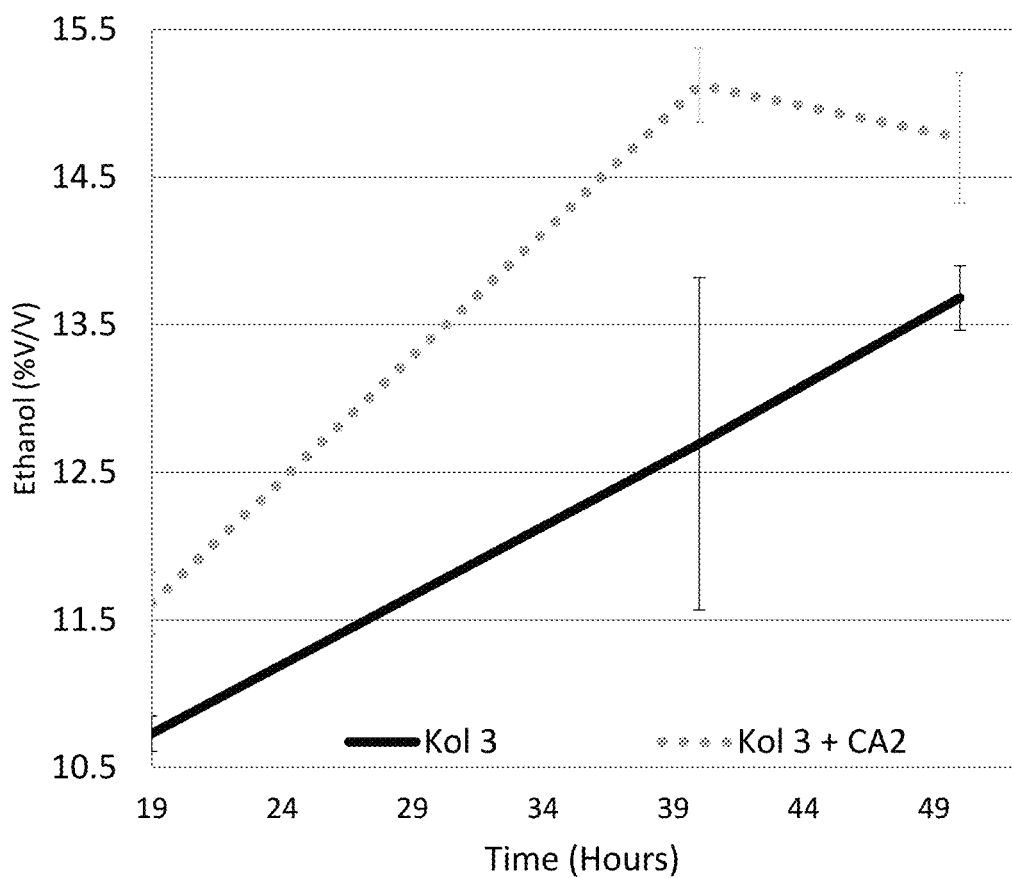
FIG. 10 presents a graph with ethanol production by commercial yeast strain Kol-Excel-3 with and without inoculation of the selected isolate CA2.

Furthermore, as we suggest an "all-included" kit containing a yeast strain combined with beneficial bacterial isolate. We tested this yeast-bacteria combination by adding isolate CA2 to the fermentation of one yeast from our collection, Kol-Excel-3. Fermentations were conducted under the absence of glucoamylase and antibiotics, this time with no deliberate contamination of damaging bacteria. The result demonstrates that isolate CA2 was able to enhance ethanol production of strain Kol-Excel-3 by a total of 1% (V/V) (FIG. 10).

Bacterial impact on ethanol production was determined with and without the addition of isolate CA2 to digested corn fermentation with no antibiotics, no glucoamylase, and 0.072% (w/v) urea. Fermentations were conducted in biological duplicates at 32.5° C., 160 RPM, for 50 hours, in a microaerophilic environment.

Example 10

Cellulase Activity

Corn contain cellulose which potentially could be used for ethanol production. Bioethanol producers frequently add exogenous cellulase to fermentations to ferment the cellulosic sugars hidden in the corn kernel fiber (generation 1.5G) and to increase ethanol yields. Cellulosic ethanol may be also produced in a second generation (2G) process uses sugars found in lignocellulosic biomass (agricultural residues, lignocellulosic crops, etc.). Therefore, bacterial strains possessing cellulase activity are of great importance for the exploitation of organic matter for biofuel, alongside to the described starch and gelatinase abilities.

Figures 11A, 11B:
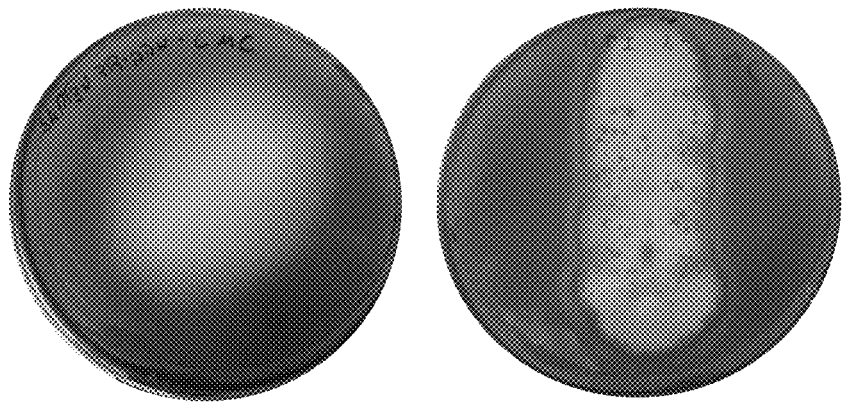
FIGS. 11A-11B presents examples of cellulase activity test. 11A) Strong positive activity for isolate CI (*P. acidilactici*), ranked 5; 11B) weak positive activity for control strain Bti, ranked 1. Plates were incubated at 37° C. for 48 hours, then kept at RT for 5 days and stained.

Assessing cellulase activity: Bacterial and yeast strains were inoculated onto Carboxymethylcellulose (CMC) agar plates (0.5% CMC, 0.4% Bacto-yeast extract, 1% malt extract, 1.2% Bacto-agar, pH=7.2). The plates were incubated for 48 hours at 37° C. and 5 days at RT. Following incubation time, the plates were stained with 5 ml of 0.1% Congo red solution for 30 minutes. The plates were then washed with distilled water, exposed to 5 ml of 1M NaCl for 5 minutes, washed again with distilled water and finally 5 ml of 5% acetic acid were added for 5 minutes. The congo red stains CMC, while areas with no CMC remain white hence indicating cellulase activity (FIG. 11A-B). Strain CI, previously isolated from corn fermentation and identified through rpoB and 16s sequencing as *Pediococcus acidilactici*, served as positive control. *B. cereus* ATCC 11778 and *B. subtilis* ATCC 6633 served as negative controls, as no cellulose activity was reported hitherto.

Table 4. Strains ranked on a scale of 0 to 5 for cellulose degradation ability

TABLE 4

Cellulase activity ranking in a scale of 0 to 5.

| Isolate | Rank | Isolate | Rank |
|---|---|---|---|
| 4 | 1 | CH2 | 1 |
| 4-9 | 1 | AB1 | 2 |
| 4-12 | 1 | AU1 | 3 |
| 8 | 0 | F3 | 2 |
| CN1 | 2 | KLU1 | 0 |
| CA2 | 3 | KLU3 | 0 |
| NN1 | 2 | B. cereus ATCC 11778 | 0 |
| NN4 | 2 | B. subtilis ATCC 6633 | 0 |
| APH1 | 0 | CI | 5 |
| APH2 | 0 | Bti | 1 |
| BL1 | 0 | Btk | 2 |
| SEF1 | 1 | OMW1 | 0 |
| SM3 | 0 | OMW2 | 0 |
| "Probit" pesticide | 2 | Bacillus megatevioil VS1 | 2 |
| Bacillus simplex SHB26 | 2 | Bacillus toyonensis | 2 |
| Serratia plymuthica | 2 | Natto | 1 |
| Bacillus thuringie- nsis HD73 | 3 | | |
| Bacillus ceveous AH621 | 2 | | |

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

What is claimed is:

1. A fermentation method comprising: contacting (i) at least one non-pathogenic hydrolase-secreting bacteria, and (ii) at least one non-pathogenic fermenting microorganism with a fermentable biomass to obtain a fermentation composition characterized by a pH in a range between 3.8 and 7,
and maintaining the fermentation composition under fermentable conditions suitable for producing a product alcohol; wherein:
a concentration of the hydrolase-secreting bacteria within the fermentation composition is between $1\times10^3$ and $1\times10^9$ Colony forming Units (CFU)/ml;
a ratio between the hydrolase-secreting bacteria and the fermenting microorganism is from 1:5 to 1:1000; and wherein said method is for increasing a concentration of the product alcohol within the fermentation composition by at least 0.1% (V/V), as compared to a similar fermentation composition devoid of the hydrolase-secreting bacteria;
wherein said product alcohol is ethanol;
wherein said fermentable biomass is selected from the group consisting of: corn grain, corn cobs, corn husks, corn stover, wheat, wheat straw, barley, barley straw, hay, and rice straw including any combination thereof;
wherein said fermenting microorganism is a yeast;
wherein the hydrolase-secreting bacteria is of genus Bacillus and is characterized by: (i) antipathogenic activity comprising growth inhibition of lactic acid bacteria and
(ii) ethanol tolerance of at least 7% v/v; and wherein the hydrolase-secreting bacteria is selected from the group consisting of: an amylase-secreting bacteria, a protease-secreting bacteria, a cellulase-secreting bacteria, and a combination thereof.

2. The method of claim 1, wherein said fermentable conditions comprise a temperature between 28 and 37° C. and anaerobic conditions.

3. The method of claim 1, wherein said contacting comprises a concentration of the hydrolase-secreting bacteria and of the fermenting microorganism within the fermentation composition between $1\times10^6$ and $1\times10^9$ CFU/ml.

4. The method of claim 1, wherein the hydrolase-secreting bacteria is said amylase-secreting bacteria.

5. The method of claim 1, further comprising providing to the fermentation composition enzymes that are added to the fermentation.

6. The method of claim 5, wherein said enzyme preparation comprises an enzyme selected from glucoamylase, alpha-amylase, cellulase, protease, or any combination thereof.

7. The method of claim 1, wherein said method is devoid of adding an antibiotic to said fermentation composition.

8. The method of claim 1, wherein said yeast is selected from genera Saccharomyces, Pichia or a combination thereof.

9. A method comprising simultaneously contacting (i) at least one non-pathogenic hydrolase-secreting bacteria, and (ii) at least one non-pathogenic fermenting microorganism with a fermentable biomass to obtain a fermentation composition characterized by a pH in a range between 4.5 and 7,
and maintaining the fermentation composition under fermentable conditions suitable for producing a product alcohol; wherein:
a concentration of the hydrolase-secreting bacteria within the fermentation composition is between $1\times10^3$ and $1\times10^9$ Colony forming Units (CFU)/ml;
a ratio between the hydrolase-secreting bacteria and the fermenting microorganism is from 1:5 to 1:1000; and wherein said method is for increasing a concentration of the product alcohol within the fermentation composition by at least 0.1% (V/V), as compared to a similar fermentation composition devoid of the hydrolase-secreting bacteria;
wherein said product alcohol is ethanol; wherein said method is devoid of adding an antibiotic to said fermentation composition;
wherein said fermentable biomass is selected from the group consisting of: corn grain, corn cobs, corn husks, corn stover, wheat, wheat straw, barley, barley straw, hay, lignocellulosic biomass, and rice straw including any combination thereof;
wherein said fermenting microorganism is a yeast;
wherein the hydrolase-secreting bacteria is of genus Bacillus and is characterized by: (i) antipathogenic activity comprising growth inhibition of lactic acid bacteria and (ii) ethanol tolerance of at least 7% v/v; and wherein the hydrolase-secreting bacteria is selected from the group consisting of: an amylase-secreting bacteria, a protease-secreting bacteria, a cellulase-secreting bacteria, and a combination thereof.

10. The method of claim 9, wherein said method is further devoid of adding glucoamylase to said fermentation composition.

* * * * *